United States Patent [19]

Ravikumar

[11] Patent Number: 5,629,152
[45] Date of Patent: May 13, 1997

[54] TRISUBSTITUTED β-LACTAMS AND OLIGO β-LACTAMAMIDES

[75] Inventor: Vasulinga Ravikumar, Carlsbad, Calif.

[73] Assignee: Isis Pharmaceuticals, Inc., Carlsbad, Calif.

[21] Appl. No.: 283,591

[22] Filed: Aug. 1, 1994

[51] Int. Cl.⁶ .............................. C12Q 1/68; C12P 19/34; C07H 21/04; A61K 48/00
[52] U.S. Cl. .............................. 435/6; 435/91.1; 536/24.5; 536/24.3; 514/44
[58] Field of Search .............................. 435/6, 91.1, 5; 526/264; 514/44, 536, 24.3; 536/24.5, 23.1, 24.3–24.33; 260/326.5

[56] References Cited

U.S. PATENT DOCUMENTS

| | | | |
|---|---|---|---|
| 4,188,478 | 2/1980 | Goebel | 528/314 |
| 5,359,044 | 10/1994 | Cook et al. | 536/23.1 |
| 5,376,529 | 12/1994 | Van Ness | 435/6 |
| 5,391,667 | 2/1995 | Dellinger | 526/264 |

FOREIGN PATENT DOCUMENTS

| | | |
|---|---|---|
| WO90/02749 | 3/1990 | WIPO. |
| WO92/20703 | 11/1992 | WIPO. |
| WO92/20702 | 11/1992 | WIPO. |
| WO93/25706 | 12/1993 | WIPO. |

OTHER PUBLICATIONS

Bodanszky et al. "Active Esters and Resins in PEptide Synthesis" Chem. Ind. 32: 1423–1424 1964.
Yajima et al., "Trifluoromethanesulfonic Acid as a Deprotecting Reagent in Peptide Chemistry", J. Soc. Chem. Comm., 1974 3: 107–108 1974.
Egholm et al, "Peptide Nucleic Acids Containing Adenine or Guanine Recognize Thymine and Cytosine in Complementary DNA seqeunces" J. Chem. Soc. Chem. Comm. 9: 800–801 1993.
Tam et al., "Improved Synthesis of 4–(Boc–aminoacycloxymethylphenylacetic Acids for Use in Solid Phase peptide Synthesis", 12: 955–957 1979.
Anderson, George W. and McGregor, "t–Butyloxycarbonylamino Acids and Their Use in Peptide Synthesis" J. Am. Chem. Soc., 1957, 79: 6180–6183.
Atherton, Eric et al., "Peptide Synthesis. Part 2. Procedures for solid–phase Synthesis Using N$^\alpha$–Fluorenylmethoxycarbonylamino–acids on Polyamide Supports. Synthesis of Substance P and of Acyl Carrier Protein 65–74 Decapeptide", J.C.S. Perkin, 1981, 1: 538–546.
Atherton et al., "The Polyamide Method of Solid Phase Peptide and Oligonucleotide Synthesis", Bioorg. Chem. 1979, 8: 351–370.
Atherton et al., "Polyamide Supports for Polypeptide Synthesis", J. Am. Chem. Soc., 1975, 97: 6584.
Atherton et al., "A Physically Supported Gel Polymer for Low Pressure, Continuous Flow Solid Phase Reactions. Application to Solid Phase Peptide Synthesis", J. Chem. Soc. Chem. Commun., 1981, 21: 1151–1152.

Barany, et al., "A New Amino Protecting Group Removable by Reduction. Chemistry of the Dithiasuccinoyl (Dts) Function" J. Am. Chem. Soc., 1977, 99: 7363–7365.
Barany and Merrifield in "The Peptides" vol. 2, Academic Press, New York, 1979, pp. 1–284.
Barany, et al., "Solid–phase Peptide Synthesis: a Silver Anniversary Report" Int. J. Peptide Protein Res., 1987, 30: 705–739.
Barton et al., "Solid–Phase Synthesis of Selectively Protected Peptides for Use as Building Units in the Solid–Phase Synthesis of Large Molecules", J. Am. Chem. Soc., 1973, 95: 4501–4506.
Bayer and Jung, "A New Support for Polypeptide Synthesis in Columns" Tetrahedron Lett., 1970, 11: 4503–4505.
Berg, et al., "Long–Chain Polystyerene–Grafted Polyethylene Film Matrix: A New Support for Solid–Phase Peptide Synthesis" J. Am. Chem. Soc., 1989, 111: 8024–8026.
Blackwell et al., "Sequence–Specific DNA Binding by the c–Myc Protein" Science 1990, 250: 1149–1151.
Bodanszky, "Principles of Peptide Synthesis", Springer–Verlag, Berlin–New York 1984, pp. 1–193.
Bodanzsky, "Synthesis of Peptides by Aminolysis of Nitrophenyl Esters" Nature, 1955, 175: 685.
Brady et al., "Some Novel, Acid–Labile Amine Protecting Groups", J. Org. Chem. 1977 42: 143–146.
Carpino, "Oxidative Reactions of Hydrazines. IV. Elimination of Nitrogen from 1,1–Disubstituted–2–arenesulfonhydrazides$^{1-4}$", J. Am. Chem. Soc., 1957, 79: 4427–4431.
Carpino and Han, "The 9–Fluorenylmethoxycarbonyl Function, a New Base–Sensitive Amino–Protecting Group", J. Am. Chem. Soc., 1970, 92: 5748–5749.
Carpino, "The 9–Fluorenylmethoxycarbonyl Amino–Protecting Group" J. Org. Chem., 1972, 37: 3404–3409.
Cullen, B.R., "The HIV–1 Tat Protein: An RNA Sequence–Specific Processivity Factor?", Cell 1990, 63: 655–657.
Eichler, Jutta et al., "Application of Cellulose Paper As Support Material in Simultaneous Solid Phase Peptide Synthesis" Collect. Czech. Chem. Commun., 1989, 54: 1746–1752.
Franza, et al., "Characterization of Cellular Proteins Recognizing the HIV Enhancer Using a Microscale DNA–Affinity Precipitation Assay", Nature 1987, 330: 391–395.

(List continued on next page.)

Primary Examiner—Stephanie W. Zitomer
Assistant Examiner—Dianne Rees
Attorney, Agent, or Firm—Woodcock Washburn Kurtz MacKiewicz & Norris

[57] ABSTRACT

Novel β-lactam monomers bearing various functional groups are prepared. The novel β-lactam monomers can be joined into oligomeric compounds via standard peptide linkages. Useful functional groups include nucleobases as well as polar groups, hydrophobic groups, ionic groups, aromatic groups and/or groups that participate in hydrogen bonding. The oligomeric compounds are useful as diagnostic and research reagents.

20 Claims, No Drawings

OTHER PUBLICATIONS

Fridkin, et al., "A Synthesis of Cyclic Peptides Utilizing High Molecular Weight Carriers", *J. Am. Chem. Soc.*, 1965, 87: 4646–4648.

Geysen, et al., "Use of Peptide Synthesis to Probe Viral Antigens for Epitopes to a Resolution of a Single Amino Acid", *Proc. Natl. Acad. Sci. USA*, 1984, 81: 3998–4002.

Gilmore, T.D. and Temin H.M., "Different Localization of the Product of the v–rel Oncogene in Chicken Fibroblasts and Spleen Cells Correlates with Transformation by REV–T", *Cell* 1986, 62: 791–800.

Gorman, Jeffrey J., "An Apparatus for Simultaneous Manual Solid–Phase Synthesis of Multiple Peptide Analogs" *Anal. Biochem.*, 1984, 136: 397–406.

Hahn, Karl W. et al., "Design and Synthesis of a Peptide Having Chymotrypsin–Like Esterase Activity" *Science*, 1990, 248: 1544–1547.

Haas, et al., "Adamantyloxycarbonyl, a New Blocking Group. Preparation of 1–Adamantyl Chloroformte" *J. Am. Chem. Soc.*, 1966, 88: 1988–1992.

Holm and Meldal, in *"Proceedings of the 20th European Peptide Symposium"*, G. Jung and E. Bayer, eds., Walter de Gruyter & Co., Berlin, 1989 pp. 208–210.

Houghten, R., "General Method for the Rapid Solid–phase Synthesis of Large Numbers of Peptides: Specificity of Antigen–Antibody Interaction at the Level of Individual Amino Acids" *Proc. Natl. Acad. Sci. USA*, 1985, 82: 5131–5135.

Jones, "Hydrogenation of Protected Leucine Enkephalin From a Resin During Solid Phase Synthesis" *Tetrahedron Lett.* 1977 18: 2853–2856.

Kent and Merrifield, "Preparation and Properties of tert–Butyloxycarbonylaminoacyl–4–(oxymethyl) phenylacetamidomethyl–(Kel F–g–styrene) Resin, an Insoluble, Noncrosslinked Support for Solid Phase Peptide Synthesis" *Israel J. Chem.* 1978, 17: 243–247.

Konig, et al., König and Geiger, "Racemisierung bei Peptidsynthesen" *Chem. Ber.*, 1970, 103: 2024–2033.

König et al., "Autoregulation of fos: the dyad symmetry element as the major target of repression" *EMBO Journal* 1989, 8: 2559–2566.

Kovacs, J. et al., "Glutamic and Aspartic Anhydrides. Rearrangement of N–Carboxyglutamic 1,5–Anhydride to the Leuchs'Anhydride and Conversion of the Latter to Pyroglutamic Acid" *J. Am. Chem. Soc.* 1963 85: 1839–1844.

Krchnak, et al., "Continuous–Flow Solid–Phase Peptide Synthesis" *Tetrahedron Lett.*, 1987, 28 4469–4472 Krchnak, et al., Multiple Continuous–Flow Solid–Phase Peptide Synthesis *Int. J. Peptide Protein Res.*, 1989, 33: 209–213.

Kupryszewski, "O Estrach Chlorofenylowych Aminokwasow. II. Synteza Peptydow Poprzez Aminolize Aktywnych Estrow 2,4,6–Trojchlorofenylowych N–chronionych Aminokwasow" *Rocz. Chem.*, 1961, 35: 595–600.

Lebl and Eichler, "Simulation of Continuous Solid Phase Synthesis: Synthesis of Methionine Enkephalin and its Analogs" Peptide Res. 1989, 2: 297–300.

Li, et al., "The Synthesis of a Protein Possessing Growth––Promoting and Lactogenic Activities" *J. Am. Chem. Soc.*, 1970, 92: 7608–7609.

McKay, et al., "New Amine–Masking Groups for Peptide Synthesis" *J. Am. Chem. Soc.*, 1957, 79: 4686–4690.

Merrifield, "Solid Phase Peptide Synthesis. I. The Synthesis of a Tetrapeptide" *J. Am. Chem. Soc.*, 1963, 85: 2149–2154.

Merrifield, B., "Solid Phase Synthesis", *Science*, 1986, 232: 341–347.

Mitchell, Alexander et al., "Preparation of Aminomethyl–Polystyrene Resin by Direct Amidomethylation" *Tetrahedron Lett.*, 1976, 42: 3795–3798.

Mitchell and Merrifield, "Occurrence of N–Alkylation during the Acidolytic Cleavage of Urethane Protecting Groups" *J. Org. Chem.*, 1976, 41: 2015–2019.

Mutter and Bayer, "Rapid Procedure for Liquid–Phase Peptide Synthesis: The Crystallization Method" *Angew. Chem., Int. Ed. Engl.*, 1974, 13: 88–89.

Nefkens, et al., "A Novel Activated Ester in Peptide Synthesis" *J. Am. Chem. Soc.*, 1961, 83: 1263.

Nisen, P., "Enhanced Expression of the N–myc Gene in Wilms' Tumors" *Cancer Research* 1986, 46: 6217–6222.

Parr and Grohmann, "Solid–Phase Peptide Synthesis on an Inorganic Matrix having Organic Groups on the Surface", *Agnew Chem. Internat. Edit.* 1972 11(4): 314–315.

Pietta and Marshall, "Amide Protection and Amide Supports in Solid–Phase Peptide Synthesis" *J. Chem. Soc.*, 1970, 11 650–651.

Pless and Boissonnas, "176. Uber die Geschwindigkeit der aminolyse von verschiedenen neuen, aktivierten, N–geschutzten α–Aminosaure–phenylestern, insbesondere 2,4, 5–Trichlorphenylestern$^1$)", *Helv. Chim. Acta*, 1963, 176: 1609–1625.

Pollack et al., "Selective Chemical Catalysis by and Antibody", *Science*, 1986, 234: 1570–1573.

Rich and Gurwara, "Preparation of a New o–Nitrobenzyl Resin for Solid–Phase Synthesis of tert–Butyloxycarbonyl–Protected Peptide Acids" *J. Am. Chem. Soc.*, 1975 97: 1575–1579.

Rivaille, et al., "Synthesis of LH–RH Using a New Phenolic Polymer as Solid Support And BOP Reagent for Fragment Coupling" *Tetrahedron*, 1980, 36: 3413–3419.

Sakakibara, Shumpei and Shimonishi, Yasutsugu, "A New Method for Releasing Oxytocin form Fully–Protected Nonapeptides Using Anhydrous Hydrogen Fluoride" *Bull. Chem. Soc. Jpn.*, 1965, 38: 1412–1413.

Schlatter, James M. and Mazur, Robert H., "Hydrogenationin Solid Phase Peptide Synthesis. I. Removal of Product from the Resin" Tet. Letts. 1977 33: 2851–2852.

Scott et al., "The Use of Resin Coated Glass Beads in the Form of a Packed Bed for the Solid Phase Synthesis of Peptides" *J. Chrom. Sci.*, 1971, 9: 577–591.

Sheehan, John C., "A New Method of Forming Peptide Bonds" *J. Am. Chem. Soc.*, 1955, 77: 1067–1068.

Shemyakin et al., "Synthesis of Peptides in Solution on a Polymeric Support. I. Synthesis of Glycylglycyl–L–Leucylglycine" *Tetrahedron Lett.*, 1965, 27: 2323–2327.

Shokat et al., "A New Strategy for the Generation of Catalytic Antibodies" *Nature* , 1989, 338: 269–271.

Sieber and Iselin, "77. Selektive Acidolytische Spaltung von Aralkyloxycarbonyl–Aminoschutzgruppen", *Helv. Chem. Acta.*, 1968, 51: 614–622.

Spalholz et al., "Bovine Papillomavirus Transcriptional Regulation: Localization of the E2–Responsive Elements of the Long Control Region", *J. Virol.*, 1987, 61: 2128–2137.

Tam, et al., "$S_N2$ Deprotection of Synthesis Peptides with a Low Concentration of HF in Dimethyl Sulfide: Evidence and Application in Peptide Synthesis" *J. Am. Chem. Soc.*, 1983, 105: 6442–6455.

Tam, et al., "Multi–Detachable Resin Supports for Solid Phase Fragment Synthesis" *Tetrahedron Lett.*, 1979, 51: 4935–4938.

Tam, "Mechanisms for the Removal of Benzyl Protelcting Groups in Synthetic Peptides by Trifluoromethanesulfonic Acid–Trifluoroacetic Acid–Dimethyl Sulfide" *J. Am. Chem. Soc.*, 1986, 108: 5242–5251.

Tam, J. et al., "Design and Synthesis of Multidetachable Resin Supports for Solid–Phase Peptide Synthesis" *J. Am. Chem. Soc.* 1980 102: 6117–6127.

Tam, "A Gradative Deprotection Strategy for the Solid–Phase Synthesis of Peptide Amides Using P–(Acyloxy) benzhydrylamine Resin and the $S_N2$ Deprotection" *J. Org. Chem.*, 1985, 50: 5291–5298.

Tramantano, et al., "Catalytic Antibodies *Science*", 1986, 234: 1566–1570.

Tregear, "Graft Copolymers as Insoluble Supports in Peptide Synthesis" in *Chemistry and Biology of Peptides*, J. Meienhofer, ed., Ann Arbor Sci. Publ., Ann Arbor, 1972 pp. 175–178.

van Rietschoten "Simultaneous Synthesis of Two Peptide Analogs on Different Insoluble Supports in *Peptides*1974", Y. Wolman, Ed., Wiley and Sons, New York, 1975, pp. 113–116.

Wieland, et al., "Symmetrical Boc–Amino Acid Anhydrides for Economical Peptide Synthesis on a Solid Phase" *Angew. Chem., Int. Ed. Engl.*, 1971, 10: 336.

Zervas, et al., "New Methods in Peptide Synthesis. I. Tritylsulfenyl and o–Nitrophenylsulfenyl Groups as N–Protecting Groups" *J. Am. Chem. Soc.*, 1963, 85: 3660–3666.

Almarsson, O., et al., "Molecular Mechanics Calculations of the Structures of Polyamide Nucleic Acid DNA Duplexes and Triple Helical Hybrids" *Proc. Natl. Acad. Sci. USA*, 1993, 90(16):7518–7522.

Almarsson, O., et al., "Peptide Nucleic Acid (PNA) Conformation and Polymorphism in PNA–DNA and PNA–RNA hybrids". *Proc. Natl. Acad. Sci. USA*, 1993, 90(20):9542–9546.

Brown, et al., "NMR Solution Structure of a Peptide Nucleic Acid Complex with RNA" *Science*, 1994, 265:777–780.

Chen, et al., "Molecular Dynamics and NMR Studies of Single–Stranded PNA's" *Tetrahedron Lett.*, 1994, 35(29):5150–5108.

Demidov, et al., "Sequence Selective Double Strand DNA Cleavage by PNA Targeting Using Nuclease S1" *Nucleic Acids Res.*, 1993, 21(9): 2103–2107.

Demidov, et al., "Stability of Peptide Nucleic Acides in Human Serum and Cellular Extracts" *Biochem. Pharmacol.*, 1994, 48(6):1310–1313.

Dueholm, et al., "An Efficient Synthetic Approach to Boc–aminoacetaldehyde and Its Application in the Synthesis of 2–Boc–aminoethylglycine Methl Ester" *Org. Prep. Proc. Int.*, 1993, 25:457–461.

Dueholm, et al., "Peptide Nucleic Acid (PNA) with a Chiral Backbone Based on Alanine" *Bioorg. Med. Chem. Lett.*, 1994, 4(8):1077–1080.

Dueholm et al., "Synthesis of Peptide Nucleic Acids Monomers Containing the Four Natural Nucleobases: Thymine, Cytosine, Adenine and Guanine, and Their Oligomerization", 1994, *J. Org. Chem*, 59(19): 5767–5773.

Egholm, et al., "Peptide Nucleic Acids (PNA). Oligonucleotide Analogues with an Achiral Peptide Backbone" *J. Am. Chem. Soc.*, 1992, 114:1895.

Egholm, et al., "Recognition of Guanine and Adenine in DNA by Cytosine and Thymine Containing Peptide Nucleic Acids (PNA)", *J. Am. Chem. Soc.*, 1992, 114:9677–9678.

Flam, F., "Can DNA Mimics Improve on the Real Thing?" *Science*, 1993, 262:1647–1649.

Frank–Kamenetskii, M., "A Change of Backbone" *Nature*, 1991, 354(6354):505.

Griffith, et al., "Single and Bis Peptide Nucleic Acids as Triplexing Agents: Binding and Stoichiometry" *J. Am. Chem. Soc.*, 1995, 117(2):831–832.

Hyrup, et al. "Modification of the Binding Affinity of Peptide Nucleic Acids (PNA) . PNA With Extended Backbones Consisting of 2–aminoethyl–B–alanine or 3–aminopropylglycine Units" *J. Chem. Soc. Chem. Commun.*, 1993, Issue 6:518–519.

Hyrup, et al., "Structure–activity Studies of the Binding of Modified Peptide Nucleic Acids (PNA) to DNA" *J. Am. Chem. Soc.*, 1994, 116(18):7964–7970.

Kosynkina, L, et al., "A Convenient Synthesis of Chiral Peptide Nucleic Acid (PNA) Monomers" *Tetrahedron Lett.*, 1994, 35(29):5173–5176.

Lagriffoul, et al., "The Synthesis, Cooligomerization and Hybridization of a Thymine–thymine Heterodimer Containing PNA" *Bioorg. Med. Chem. Lett.*, 1994, 4(8):1081–1085.

Leijon, et al., "Structural Characterization of PNA–DNA Duplexes by NMR. Evidence for DNA in a B–like Conformation" *Biochemistry*, 1994, 33(33):9820–9825.

Mollegaard, et al., "Peptide Nucleic Acid–DNA Strand Displacement Loops as Artificial Transcription Promoters" *Proc. Natl. Acad. Sci. USA*, 1994, 91(9):3892–3895.

Nielson, et al., "Peptide Nucleic Acids (PNA). Potential Anti–Sense and Anti–Gene Agents" *Anticancer Drug Des.*, 1993, 8(1):53–63.

Nielson, P.E., "Peptide Nucleic Acids (PNA): Potential Antiviral Agents" Int'l. *Antiviral News*, 1993, 1:37–39.

Nielson, et al., "Peptide Nucleic Acids (PNA). DNA Analogues with a Polyamide Backbone" *Antisense Research and Applications, CRC Press*, 1993, pp. 363–373.

Nielson, P.E., "Peptide Nucleic Acid (PNA): A Model Structure for the Primordial Genetic Material" *Orig. Life Evol. Biosph.*, 1993, 23(5–6):323–327.

Nielson, et al., "Peptide Nucleic Acid (PNA). A DNA Mimic with a Peptide Backbone" *Bioconjugate Chem.*, 1994, 5(1):3–7.

Nielson, et al., "Sequence-specific Transcription Arrest by Peptide Nucleic Acid Bound to the DNA Template Strand", 1994, *Gene*, 149(1): 139–145.

Orum, et al., "Single Base Pair Mutation Analysis by PNA Directed PCR Clamping", *Nucleic Acids Res.*, 1993, 21(23):5332–5336.

Peffer, et al., "Strand–Invasion of Duplex DNA by Peptide Nucleic Acid Oligomers" *Proc. Natl. Acad. Sci. USA*, 1993, 90(22):10648–10652.

Rose, D.J., "Characterization of Antisense Binding Properties of Peptide Nucleic Acids By Capillary Gel Electrophoresis" *Am. Chem.*, 1993, 65(24):3545–3549.

Wittung, et al., "DNA–like Double Helix Formed by Peptide Nucleic Acid" *Nature*, 1994, 368(6471):561–563.

U.S. Ser. No. 032,852, filed Mar. 16, 1993.

U.S. Ser. No. 108,591, filed Aug. 27, 1993.

TRISUBSTITUTED β-LACTAMS AND OLIGO β-LACTAMAMIDES

FIELD OF THE INVENTION

The present invention is directed to a new class of polymeric compounds for binding to complementary DNA and RNA strands. In particular, the invention concerns compounds wherein naturally-occurring nucleobases or other nucleobase-binding moieties are covalently bound to an oligo β-lactamamide, i.e., a backbone comprising repeating units of trisubstituted β-lactams connected by amide linkages. These compounds are useful for diagnostics, research reagents and therapeutics. The present invention is also directed to processes for synthesizing such compounds, and to intermediates used in such processes.

BACKGROUND OF THE INVENTION

Oligonucleotides have been shown to interact with mRNA and other components associated with transcription. By virtue of such interaction, natural and synthetic oligonucleotides have become valuable tools for research and important agents in diagnostic, therapeutic and other applications. By virtue of their many uses, there is a demand for improved oligonucleotides, e.g. oligonucleotide analogs.

Oligonucleotides and oligonucleotide analogs have been used in a number of areas of research. In genomic research oligonucleotides have been used as probes and primers. Oligonucleotides are also useful in diagnostics because of their ability to specifically hybridize to nucleic acid sequences of interest in the etiology of a given disease. Oligonucleotides are also being tested as therapeutic moieties in the treatment of disease states in animals and man. For example, oligonucleotide therapeutic compositions have been identified that are capable of modulating expression of genes implicated in viral, fungal and metabolic diseases. It has now become routine to synthesize oligodeoxyribonucleotides and oligoribonucleotides having hundreds of base pairs (bp) by solid phase methods using commercially available, fully automatic synthesizers. Thus, oligonucleotides are of increasing importance, and have great utility in biotechnology and medical applications.

Unmodified oligonucleotides, i.e. natural phosphodiester linked oligonucleotides, are impractical for some in vivo applications because they either have short in vivo half-lives or suffer from a limited ability to penetrate cell membranes. Several variations in the polynucleotide backbone have been proposed to overcome these limitations, including the use of methylphosphonates, monothiophosphates, dithiophosphates, phosphoramidates, phosphate esters, bridged phosphoramidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives. These analogues have diverse properties, and several of these derivatives have been shown to be superior to natural oligonucleotides for particular applications.

One important oligonucleotide analogue is a class of compounds known as peptide nucleic acids (PNAs).

See PCT application PCT EP92/01219, filed May 19, 1992 and published Nov. 26, 1992 as WO 92/20702, and PCT application EP/01220, filed May 19, 1992, and published as WO 92/20703. See also U.S. application Ser. No. 108,591 filed Aug. 27, 1993, which is assigned to an assignee of this Application. Each of the foregoing applications are hereby incorporated by reference in their entirety. PNAs have enhanced hybridization to complimentary DNA and RNA strands as compared to natural oligonucleotides and most other known oligonucleotide analogues, and also have enhanced nuclease and protease stability. PNAs have uncharged, amide linked backbones instead of the charged phosphodiester backbone of oligonucleotides. This neutral backbone has proven to be especially useful in diagnostics, wherein PNAs have been hybridized to complementary DNA strands, and the resulting duplexes have been analyzed by capillary electrophoresis.

Consequently, there remains a need in the art for stable compounds that can form double-stranded, helical structures mimicking double-stranded DNA.

OBJECTS OF THE INVENTION

It is one object of the present invention to provide oligomeric compounds that mimic the double-helical structure of DNA.

It is a further object of the invention to provide compounds wherein linear, polymeric strands coordinate through hydrogen bonds to form double halices.

It is another object to provide compounds wherein naturally-occurring nucleobases or other nucleobase-binding moieties are covalently bound to a non-sugar-phosphate backbone.

It is another object to provide monomeric compounds useful in the preparation of oligomeric compounds of the invention.

It is yet another object to provide methods for the preparation of novel compounds of the invention.

SUMMARY OF THE INVENTION

Compounds of the invention include oligomeric compounds of structure I:

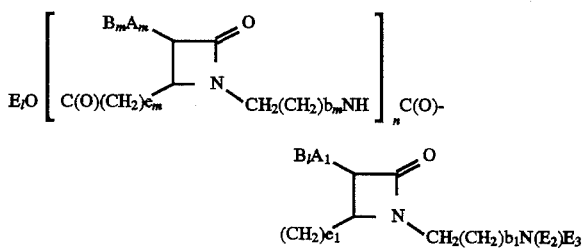

wherein $B_1$ and each $B_m$, independently, are a naturally occurring nucleobase, a non-naturally occurring nucleobase, a DNA intercalator, a nucleobase-binding group, hydrogen, hydroxyl, a ($C_1$–$C_4$)alkanoyl, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligo-β-lactamamide, a group for improving the pharmacodynamic properties of an oligo-β-lactamamide, or a reporter ligand;

$A_1$ and each $A_m$, independently, are $(CR_6R_7)_x$ where $R_6$ and $R_7$ are independently selected from the group consisting of hydrogen, alkyl, aryl, aralkyl, heteroaryl, hydroxy, alkoxy, alkylthio, $NR_3R_4$ and $SR_5$, where each of $R_3$ and $R_4$ is independently selected from the group consisting of hydrogen, alkyl, alkoxy, or alkylthio-substituted alkyl, alkoxy, alkylthio and amino; and $R_5$ is hydrogen, alkyl, hydroxy-, alkoxy-, or alkylthio- substituted alkyl, or $R_6$ and $R_7$ taken together complete an alicyclic system, wherein said alkyl groups comprise $C_1$–$C_6$ and said aryl groups comprise $C_6$–$C_{14}$;

$x$ is 0 to 10, provided that when $B_1$ or $B_m$ are hydrogen or hydroxyl, $x$ is not 0;

$E_1$ is a carboxyl protecting group or hydrogen;

$E_2$ and $E_3$, independently, are hydrogen, an amine protecting group, or taken together with N form a cyclic structure;

n is an integer from 1 to 60;

$e_1$ and each $e_m$, independently, are 0 or an integer from 1 to 6;

$b_1$ and each $b_m$, independently, are 0 or an integer from 1 to 6;

In certain preferred embodiments $B_1$ and each $B_m$ are independently selected as a naturally occurring or non naturally occurring nucleobase. In yet other preferred embodiments $e_1$, $e_m$, $b_1$, and each $b_m$ are, independently, an integer from 1 to about 4.

In other embodiments of the invention n is from 1 to about 40. A more preferred range of n is from 1 to about 20.

Compounds of the invention also include monomeric compounds of structure II:

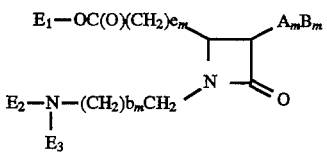

wherein $B_m$ is a naturally occurring nucleobase, a non-naturally occurring nucleobase, a DNA intercalator, a nucleobase-binding group, hydrogen, hydroxyl, a $(C_1$–$C_4)$alkanoyl group, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of a lactamamide, a group for improving the pharmacodynamic properties of a lactamamide, or a reporter ligand;

$A_m$ is $(CR_6R_7)_x$ where $R_6$ and $R_7$ are independently selected from the group consisting of hydrogen, alkyl, aryl, aralkyl, heteroaryl, hydroxy, alkoxy, alkylthio, $NR_3R_4$ and $SR_5$, where each of $R_3$ and $R_4$ is independently selected from the group consisting of hydrogen, alkyl, alkoxy, or alkylthio-substituted alkyl, alkoxy, alkylthio and amino; and $R_5$ is hydrogen, alkyl, hydroxy-, alkoxy-, or alkylthio-substituted alkyl, or $R_6$ and $R_7$ taken together complete an alicyclic system, wherein said alkyl groups comprise $C_1$–$C_6$ and said aryl groups comprise $C_6$–$C_{14}$;

$x$ is 0 to 10, provided that when $B_m$ is hydrogen or hydroxyl, $x$ is not 0;

$E_1$ is a carboxyl protecting group or hydrogen;

$E_2$ and $E_3$, independently, are hydrogen, an amine protecting group, or taken together with N form a cyclic structure;

$e_m$ is 0 or an integer from 1 to 6;

$b_m$ is 0 or an integer from 1 to 6;

In certain preferred embodiments $B_m$ is selected as a naturally occurring or non naturally occurring nucleobase.

In other embodiments of the invention $e_m$, and $b_m$ are independently an integer from 1 to about 4.

Also in accordance with this invention there are provided methods for preparing oligomeric compounds of the present invention. The methods include providing a polymer substrate functionalized with a chemical group capable of forming an anchoring linkage with a β-lactam of structure III;

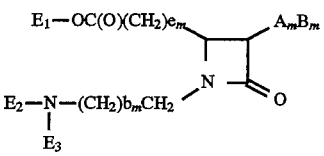

wherein $B_m$ is a naturally occurring nucleobase, a non-naturally occurring nucleobase, a DNA intercalator, a nucleobase-binding group, hydrogen, hydroxyl, a $(C_1$–$C_4)$alkanoyl, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligo-β-lactamamide, a group for improving the pharmacodynamic properties of an oligo-β-lactamamide, or a reporter ligand;

$A_m$ is $(CR_6R_7)_x$ where $R_6$ and $R_7$, independently, are selected from the group consisting of hydrogen, alkyl, aryl, aralkyl, heteroaryl, hydroxy, alkoxy, alkylthio, $NR_3R_4$ and $SR_5$, where each of $R_3$ and $R_4$ is independently selected from the group consisting of hydrogen, alkyl, alkoxy, or alkylthio-substituted alkyl, alkoxy, alkylthio and amino; and $R_5$ is hydrogen, alkyl, hydroxy-, alkoxy-, or alkylthio-substituted alkyl, or $R_6$ and $R_7$ taken together complete an alicyclic system, wherein said alkyl groups comprise $C_1$–$C_6$ and said aryl groups comprise $C_6$–$C_{14}$;

$x$ is 0 to 10, provided that when $B_m$ is hydrogen or hydroxyl, $x$ is not 0;

$E_1$ is a carboxyl protecting group and $E_2$ and $E_3$ are hydrogen; or $E_1$ is hydrogen and one of $E_2$ and $E_3$ is an amine protecting group and the other is hydrogen or together with N $E_2$ and $E_3$ form a cyclic structure;

$e_m$ is 0 or an integer from 1 to 6; and $b_m$ is 0 or an integer from 1 to 6.

The methods further include coupling the polymer with a β-lactam having structure III through the anchoring linkage, deprotecting the coupled β-lactam to generate a free amino or a free carboxyl group, and reacting the free amino group or the free carboxyl group with a β-lactam having structure III to form a peptide chain.

Further methods for the preparation of oligomeric compounds of the invention include removing the protecting group from the β-lactam to generate a terminal unprotected group on the peptide chain followed by reacting the unprotected group on the peptide chain with a further β-lactam having structure III to lengthen the peptide chain.

In one embodiment of the invention the steps of removing the terminal protecting group on the growing peptide chain and reacting the resulting unprotected group with a further β-lactam having structure III to lengthen the peptide chain is repeated a plurality of times. In another embodiment of the invention $E_1$ is hydrogen and one of $E_2$ and $E_3$ is an amine protecting group and the other is hydrogen or together with N, $E_2$ and $E_3$ form a cyclic structure. In a further embodiment the growing chain is cleaved from the polymer substrate by cleaving the anchoring linkage.

Preferred polymer substrates are polystyrene, polyacrylamide, silica, a composite material, cotton, or a derivative thereof.

In further embodiments of the invention the chemical group capable of forming the anchoring linkage is chloro-, bromo- and iodo-substituted alkyl, amino-substituted alkyl, amino and aryl-substituted alkyl, amino- and alkylaryl-substituted alkyl, hydroxy-substituted alkyl, or a derivative thereof having a spacer group that can be cleaved substantially without degradation of the polypeptide.

In a preferred embodiment of the invention the chloro-substituted alkyl is chloromethyl, amino-substituted alkyl is aminomethyl, amino- and alkyl-substituted aryl is α-aminobenzyl, amino- and alkylaryl-substituted alkyl is selected from the group consisting of α-amino-3- and α-amino-4-methylbenzyl, and hydroxy-substituted alkyl is hydroxymethyl.

In still further embodiments of the invention the chemical group is derived from an amino-containing moiety selected from amino-substituted alkyl, amino- and aryl substituted alkyl, and amino- and alkylaryl-substituted alkyl and the chemical group includes a spacer group derived from the group consisting of 4-(haloalkyl)aryl-lower alkanoic acids, BOC-aminoacyl-4-(oxymethy) aryl-lower alkanoic acids, N-BOC-p-acylbenzhydrylamines, N-BOC-4'-(lower alkyl)-p-acylbenzhydryl-amines, N-BOC-4'-(lower alkoxy)-p-acylbenzhydrylamines, and 4-hydroxymethylphenoxy-lower alkanoic acids.

In accordance with the present invention there is provided an oligomeric compound comprising β-lactam monomers having N-1, C-3, and C-4 positions substituted with covalently bonded functional groups. One of the N-1, C-3, or C-4 positions is substituted with one of a tethered or untethered carboxyl group. Another of the N-1, C-3, or C-4 positions is substituted with one of a tethered or untethered functional group and the remaining of the N-1, C-3, or C-4 positions is substituted with a tethered amine group. The β-lactam monomers are joined via amide linkages formed from the tethered amine group of one β-lactam monomer and the carboxyl group from a further β-lactam monomer.

In a preferred embodiment of the invention the terminal carboxyl group on one end of the final oligomeric compound is protected. In other preferred embodiments the tethered amine group not involved in amide linkages is protected, unprotected, or capped with a BOC-glycine group.

In one embodiment of the invention one of the covalently bonded functional groups from each of the β-lactam monomers is independently a naturally occurring nucleobase, a non-naturally occurring nucleobase, a DNA intercalator, a nucleobase-binding group, hydrogen, hydroxyl, a $(C_1-C_4)$ alkanoyl, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligo-β-lactamamide, a group for improving the pharmacodynamic properties of an oligo-β-lactamamide, or a reporter ligand.

In other embodiments of the invention the tethered or untethered functional group from each of the β-lactam monomers is independently covalently bonded to each of the β-lactam monomers via a tether. The tether is selected from $(CR_6R_7)_x$ where $R_6$ and $R_7$ are independently selected from the group consisting of hydrogen, alkyl, aryl, aralkyl, heteroaryl, hydroxy, alkoxy, alkylthio, $NR_3R_4$ and $SR_5$, where each of $R_3$ and $R_4$ is independently selected from the group consisting of hydrogen, alkyl, alkoxy, or alkylthio-substituted alkyl, alkoxy, alkylthio and amino; and $R_5$ is hydrogen, alkyl, hydroxy-alkoxy-, or alkylthio- substituted alkyl, or $R_6$ and $R_7$ taken together complete an alicyclic system; where $_x$ is 0 to 10, provided that when $B_m$ is hydrogen or hydroxyl, $_x$ is not 0.

In a further preferred embodiment of the invention the functional groups covalently bonded to the β-lactam monomers are naturally occurring nucleobases or non naturally occurring nucleobases.

In another embodiment of the invention the oligomeric compound is from 1 to about 60 of the β-lactam monomers in length. In a preferred embodiment the oligomeric compound is from 1 to about 40 of the β-lactam monomers in length. In yet a further preferred embodiment the oligomeric compound is from 1 to about 20 of the β-lactam monomers in length.

In yet a further embodiment of the invention the tethered or untethered carboxyl group and the tethered amino group from each of the β-lactam monomers is independently tethered using a $C_1-C_6$ alkyl tether. In a more preferred embodiment the tethered or untethered carboxyl group and the tethered amino group from each of the β-lactam monomers is independently tethered using a $C_1-C_4$ alkyl tether.

In a further embodiment of the invention the amino group is covalently bonded to one of the C-4 or C-3 positions of the β-lactams without a tether.

DESCRIPTION OF PREFERRED EMBODIMENTS

The monomeric compounds of the invention are trisubstituted β-lactam moieties which are substituted at the N-1, C-3, and C-4 positions with tethered or untethered functional groups, which have the formula:

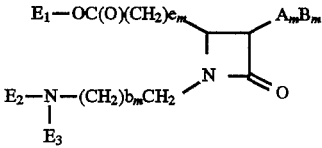

II wherein $A_m$, $B_m$, $E_1$, $E_2$, $E_3$, $e_m$, and $b_m$ have the same meaning as defined above.

Preferred substitutions at the C-3 position include naturally occurring nucleobases, non naturally occurring nucleobases and other functional moieties. Naturally occurring nucleobases are defined herein as those which occur naturally in living entities, including thymine, adenine, cytosine, guanine, and uracil. Non-naturally occurring nucleobases are synthetic molecular moieties which mimic the biological or chemical function of naturally occurring nucleobases with respect to their base-recognition and binding properties.

The functional moieties $B_m$ may be tethered through an $A_m$ group, which may be selected to be either a functional moiety, or, more preferably, a spacer or tether moiety for a functional $B_m$ group.

Preferred substitutions at the C-4 position of the monomeric compounds of the invention include carboxyl groups, which may be protected by a suitable protecting group or be activated, and which may optionally be bound through a tether of up to 6 methylene groups.

The trisubstituted monomeric β-lactamamides of the invention are preferably substituted at the N-1 position by primary aminoalkyl groups, which may bear amino protecting groups. The alkyl portions of the aminoalkyl groups are preferably methylene tethers from two to eight methylene groups in length.

As used herein, a reporter ligand is a molecule or enzyme that has physical or chemical properties that allow it to be identified in gels, fluids, whole cellular systems, broken cellular systems and the like utilizing physical properties such as spectroscopy, radioactivity, colorimetric assays, fluorescence, and specific binding. Particularly useful as reporter molecules are biotin and fluorescein dyes. Particularly useful as reporter enzymes are alkaline phosphatase and horse-radish peroxidase. Reporter groups such as biotin, and various fluorophores may be attached to compounds of the present invention to effect signal amplificaition, facilitating diagnostic ends.

Groups that enhance pharmacodynamic properties of trisubstituted β-lactams and oligo β-lactamamides include groups that improve uptake, enhance resistance to degradation, and/or strengthen sequence-specific interaction with a target molecule. Groups that enhance pharmacokinetic properties of trisubstituted β-lactams and oligo β-lactamamides include groups that improve uptake, distribution, metabolism or excretion. A representative list of groups that are expected to enhance the pharmacodynamic and or pharmacokinetic properties of trisubstituted β-lactams and oligo β-lactamamides includes alkyl chains, polyamines, ethylene glycols, polyamides, aminoalkyl chains, amphipathic moieties, and intercalators.

Heterocyclic moieties according to the invention include but are not limited to nitrogen heterocycles such as imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Imidazole groups are especially preferred.

Aryl groups according to the invention include but are not limited to substituted and unsubstituted aromatic hydrocarbyl groups such as phenyl and naphthyl groups. Aralkyl groups are groups having both aryl and alkyl functionality, such as benzyl and xylyl groups, wherein the chemical linkage to the β-lactamamids is through the alkyl portion of the aralkyl group. Alkaryl groups are groups having both aryl and alkyl functionality, wherein the aryl portion thereof is bound to the β-lactamamide.

A representative synthesis of trisubstituted β-lactams of the invention appears below in Scheme I:

SCHEME I

NH$_2$(CH$_2$)b$_m$CN
(1)

(BOC)OC(O)C(CH$_3$)$_3$ $\longrightarrow$ (BOC)NH(CH$_2$)b$_m$CN
(2) (3)

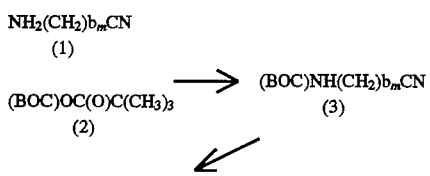

-continued
SCHEME I (BOC)NH(CH$_2$)b$_m$CH$_2$NH$_2$
(4)

+ $\longrightarrow$ (BOC)NH(CH$_2$)b$_m$CH$_2$NCH(CH$_2$)e$_m$C(O)OCH$_3$
(6)

CH$_3$OC(O)(CH$_2$)e$_m$C(O)H
(5) +

A$_m$
B$_m$ $\xrightarrow{(8)}_{\text{optional}}$ B$_m$A$_m$ $\longrightarrow$ B$_m$A$_m$CH$_2$C(O)OCH$_3$
(7) (9) (11)

BrCH$_2$C(O)OCH$_3$
(10)

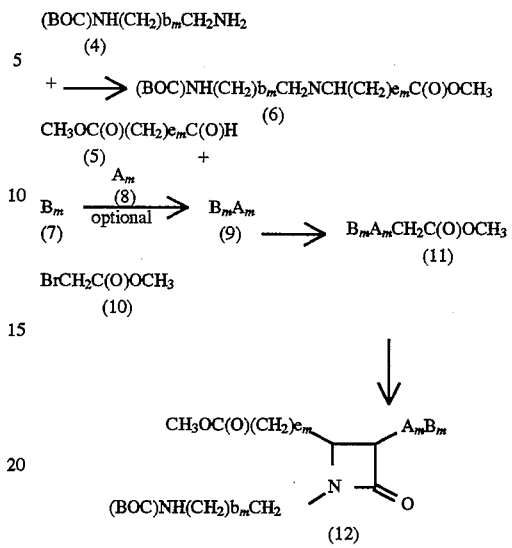

Aminoalkylcyano compound 1 is reacted with an amino blocking group reagent di-t-butyldicarbonate 2 under conditions to give the protected aminoalkylcyano compound 3. The protected aminoalkylcyano compound 3 is hydrogenated under appropriate conditions to give the protected aminoalkylamino compound 4. The protected aminoalkylamino compound is reacted with an aldehyde alkyl methylester 5 to give the imine compound 6.

In a separate synthesis optionally protected B$_m$ 7 is optionally reacted with optionally protected A$_m$ 8 to give B$_m$A$_m$ 9, which is further reacted with a methyl halo ester 10 to give ester 11. Compound 6 and compound 11 are then condensed and cyclized via an acid chloride imine condensation to give the trisubstituted fully protected β-lactam 12.

It may be seen that a large number of diverse structures may be synthesized by appropriate choice of starting reactants. The use of different A$_m$ groups will modify the distance from the β-lactam backbone to the Base moiety (B$_m$). When A$_m$ is not incorporated as a separate entity, it may still be incorporated by altering the ester compound 10. A small alkyl chain can be incorporated as for instance using methyl bromoproprionate to give A$_m$ equal to CH$_2$ or using methyl bromobutyrate as the ester to give A$_m$ equal to C$_2$H$_4$. Altering the number of methylene spacing groups (varying e$_m$ and b$_m$) affords flexibility in the overall length of the final oligomer.

The trisubstituted β-lactam of Scheme I is merely representative of the large number of trisubstituted β-lactams of the invention. Those skilled in the art will recognize that β-lactams according to the invention having functional, carboxyl and aminoalkyl substituents at alternate positions on the β-lactam ring can be synthesized according to the general method of Scheme I, by appropriate choice of starting reactants.

Also provided in preferred embodiments of the invention are oligomeric compounds having formula:

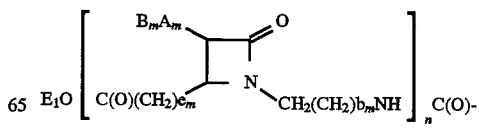

-continued

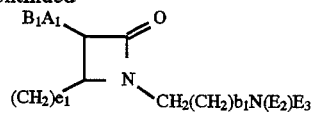

wherein $A_m$, $B_m$, $A_1$, $B_1$, $E_1$, $E_2$, $E_3$ $e_m$, and $b_m$ have the same meaning as defined above. These oligo-β-lactamamides of the present invention can be synthesized by Solid Phase Syntheses currently employed for polypeptides and peptide nucleic acids. The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85; 2149 and *Science*, 1986, 232i 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase oligo-β-lactamamide synthesis in accordance with the present invention.

For the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Ill., 1984). Reactions for the introduction of chloromethyl functionality (Merrifield resin; via a chloromethyl methyl ether/$SnCl_4$ reaction), aminomethyl functionality (via an N-hydroxymethylphthalimide reaction; see, Mitchell, et al., *Tetrahedron Lett.*, 1976, 17: 3795), and benzhydrylamino functionality (Pietta, et al., *J. Chem. Soc.*, 1970, 11: 650) are the most widely used. Regardless of its nature, the purpose of the functionality is normally to form an anchoring linkage between the copolymer solid support and the C-terminus of the first amino acid to be coupled to the solid support. As will be recognized, anchoring linkages also can be formed between the solid support and the amino acid N-terminus. As these methods apply to the present invention the anchoring will be to the carboxyl group or the amino group of the trisubstituted β-lactam. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention.

Preferred methods for peptide synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30: 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, BOC-aminoacyl-4-(oxymethyl)aryl-lower alkanoic acids such as BOC-aminoacyl-4 -(oxymethyl)phenylacetic acid, N-BOC-p-acylbenzhydrylamines such as N-BOC-p-glutaroylbenzhydrylamine, N-BOC-4'-lower alkyl-p-acylbenzhydrylamines such as N-BOC-4'-methyl-p-glutaroylbenzhydrylamine, N-BOC-4'-lower alkoxy-p-acylbenz-hydrylamines such as N-BOC-4'-methoxy-p-glutaroyl-benzhy-drylamine, and 4-hydroxymethylphenoxyacetic acid. One type of spacer group particularly relevant within the context of the present invention is the phenylacetamidomethyl (Pam) handle (Mitchell and Merrifield, *J. Org. Chem.*, 1976, 41: 2015) which, deriving from the electron withdrawing effect of the 4-phenylacetamidomethyl group, is about 100 times more stable than the classical benzyl ester linkage towards the BOC-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized oligo-β-lactamamide from the solid support such that the C-terminal of the oligo-β-lactamamide is in amide form, require no introduction of a spacer group. Any such functionality may advantageously be employed in the context of the present invention.

An alternative strategy concerning the introduction of spacer or handle groups is the so-called "preformed handle" strategy (see Tam, et al., *Synthesis*, 1979, 12: 955–957), which may offer complete control over coupling of the first trisubstituted β-lactam, and may exclude the possibility of complications arising from the presence of undesired functional groups not related to the oligo-β-lactamamide synthesis. In this strategy, spacer or handle groups, of the same type as described above, are reacted with the first trisubstituted-β-lactam desired to be bound to the solid support, the trisubstituted-β-lactam being N-protected and optionally protected at the other side-chains and functional moieties which are not relevant with respect to the growth of the desired oligo-β-lactamamide. Thus, in those cases in which a spacer or handle group is desirable, the first trisubstituted β-lactam to be coupled to the solid support can either be coupled to the free reactive end of a spacer group which has been bound to the initially introduced functionality (for example, an aminomethyl group) or can be reacted with the spacer-forming reagent. The spacer-forming reagent is then reacted with the initially introduced functionality. Other useful anchoring schemes include the "multidetachable" resins (Tam, et al., *Tetrahedron Lett.*, 1979, 20: 4935 and *J. Am. Chem. Soc.*, 1980, 102: 611; Tam, *J. Org. Chem.*: 1985, 50: 5291), which provide more than one mode of release and thereby allow more flexibility in synthetic design.

After attachment of the initial synthon or handle it is advantageous to perform a capping step to cap unreacted amine groups. Suitable reagents for capping include a 10% solution of N-benzyloxycarbonyl-N'-methyl-imidazole triflate in N,N-dimethylformamide. The capping step may optionally be repeated after the coupling of each monomeric synthon of the oligomer.

Suitable choices for N-protection are the tert-butyloxycarbonyl (BOC) group (Carpino, *J. Am. Chem. Soc.*, 1957, 79: 4427; McKay, et al., *J. Am. Chem. Soc.*, 1957, 79: 4686; Anderson, et al., *J. Am. Chem. Soc.*, 1957, 79: 6180) normally in combination with benzyl-based groups for the protection of side chains or functional moieties, and the 9-fluorenylmethyloxycarbonyl (Fmoc) group (Carpino, et al., *J. Am. Chem. Soc.*, 1970, 92: 5748 and *J. Org. Chem.*, 1972, 37: 3404), normally in combination with tert-butyl (tBu) for the protection of any side chains or functional moieties, although a number of other possibilities exist which are well known in conventional solid-phase peptide synthesis. Thus, a wide range of other useful amino protecting groups exist, some of which are Adoc (Hass, et al., *J. Am. Chem. Soc.*, 1966, 88: 1988), Bpoc (Sieber, *Helv. Chem. Acta.*, 1968, 51: 614), Mcb (Brady, et al., *J. Org. Chem.*, 1977, 42: 143), Bic (Kemp, et al., *Tetrahedron*, 1975, 52: 4624), the o-nitrophenylsulfenyl (Nps) (Zervas, et al., *J. Am. Chem. Soc.*, 1963, 85: 3660), and the dithiasuccinoyl (Dts) (Barany, et al., *J. Am. Chem. Soc.*, 1977, 99: 7363). In addition to such amino protecting groups, a whole range of other nonurethane-type amino protecting groups are applicable when assembling oligo-β-lactamamides. Thus, in addition to the above-mentioned amino protecting groups (or those derived from any of these groups) those skilled in the art will find useful within the context of the present invention virtually any amino protecting group which largely fulfills the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids); and (4) the protecting group must be close to quantitatively removable, without serious side reactions. Finally, the choice of protecting groups, in general, depends on the choice of the amino protecting group, since the groups protecting the functional moieties must withstand the conditions of the repeated amino deprotection cycles. This is true whether the overall strategy for chemically assembling oligo-β-lactamamides relies on, for example, differential acid stability of amino and functional moiety protecting groups (such as is the case for the above-mentioned "BOC-benzyl" approach) or employs an orthogonal, that is, chemoselective, protection scheme (such as is the case for the above-mentioned "Fmoc-tBu" approach).

Following coupling of the first trisubstituted-β-lactam, the next stage of solid-phase synthesis is the systematic elaboration of the desired oligo-β-lactamamide. This elaboration involves repeated deprotection/coupling cycles. The temporary protecting group, such as a BOC or Fmoc group, on the last-coupled amino acid is quantitatively removed by a suitable treatment, for example by acidolysis such as with trifluoroacetic acid in the case of BOC, or by base treatment such as with piperidine in the case of Fmoc, so as to liberate the N-terminal amine function.

The next desired N-protected trisubstituted-β-lactam is then coupled to the N-terminal of the last-coupled trisubstituted-β-lactam. This coupling of the C-terminal of a trisubstituted-β-lactam with the N-terminal of the last-coupled trisubstituted-β-lactam can be achieved in several ways. For example, it can be bound by providing the incoming trisubstituted-β-lactam in a form with the carboxyl group activated by any of several methods, including the initial formation of an active ester derivative such as a 2,4,5-trichlorophenyl ester (Pless, et al., *Helv. Chim. Acta*, 1963, 46: 1609), a phthalimido ester (Nefkens, et al., *J. Am. Chem. Soc.*, 1961, 83, 1263), a pentachlorophenyl ester (Kupryszewski, Rocz. Chem., 1961, 35: 595), a pentafluorophenyl ester (Kovacs, et al., *J. Am. Chem. Soc.*, 1963, 85: 183), an o-nitrophenyl ester (Bodanzsky, *Nature*, 1955, 175: 685), an imidazole ester (Li, et al., *J. Am. Chem. Soc.*, 1970, 92: 7608), and a 3-hydroxy-4-oxo-3,4-dihydroquinazoline (Dhbt-OH) ester (Konig, et al., *Chem. Bet.*, 1973, 103: 2024 and 2034), or the initial formation of an anhydride such as a symmetrical anhydride (Wieland, et al., *Angew. Chem., Int. Ed. Engl.*, 1971, 10: 336). Alternatively, the carboxyl group of the incoming trisubstituted-β-lactam can be reacted directly with the N-terminal of the last-coupled amino acid with the assistance of a condensation reagent such as, for example, dicyclohexylcarbodiimide (Sheehan, et al., *J. Am. Chem. Soc.*, 1955, 77: 1067) or derivatives thereof. Benzotriazolyl N-oxytrisdimethylaminophosphonium hexafluorophosphate (BOP), "Castro's reagent" (see, e.g., Rivaille, et al., *Tetrahedron*, 1980, 36: 3413) is recommended when assembling oligo-β-lactamamides containing secondary amino groups.

The iterative addition of monomeric subunits is carried forward until the desired oligomer is assembled. After the final monomer synthon is attached, it may be desirable in some preferred embodiments of the invention to cap the N-terminal amino group of the oligomer with glycine. Capping may be accomplished by any of the foregoing coupling chemistries using an amino-protected glycine. Such capping is routinely performed in the synthesis of peptide nucleic acids to prevent possible participation of the terminal amine moieties of PNA molecules in intra or intermolecular reactions with available carbonyl groups. Following assembly of the desired oligo-β-lactamamide, including protecting groups and glycine cap (if desired), the next step will normally be cleavage of the synthesized oligo-β-lactamamide from the solid support and deprotection of functional moieties thereon. These processes can take place substantially simultaneously, thereby providing the free oligo-β-lactamamide in the desired form.

In the above-mentioned "BOC-benzyl" protection scheme, the final deprotection of functional moieties and release of the oligo-β-lactamamide from the solid support can be carried out by the use of strong acids such as anhydrous HF (Sakakibara, et al., *Bull. Chem. Soc. Jpn.*, 1965, 38: 4921), boron tris (trifluoroacetate) (Pless, et al., *Helv. Chim. Acta*, 1973, 46: 1609), and sulfonic acids such as trifluoromethanesulfonic acid and methanesulfonic acid (Yajima, et al., *J. Chem. Soc. Chem. Comm.* 1974, 3: 107). This conventional strong acid (e.g., anhydrous HF) deprotection method, produces very reactive carbocations that may lead to alkylation and acylation of sensitive residues in the oligo-β-lactamamide. Such side-reactions are only partly avoided by the presence of scavengers such as anisole, phenol, dimethyl sulfide, and mercaptoethanol. Therefore, the sulfide-assisted acidolytic $S_N2$ deprotection method (Tam, et al., *J. Am. Chem. Soc.*, 1983, 105: 6442 and *J. Am. Chem. Soc.*, 1986, 108: 5242), the so-called "low", which removes the precursors of harmful carbocations to form inert sulfonium salts, is frequently employed in peptide synthesis, either solely or in combination with "high" methods. Less frequently, in special cases, other methods used for deprotection and/or final cleavage of the oligo-β-lactamamide-solid support bond are, for example, such methods as base-catalyzed alcoholysis (Barton, et al., *J. Am. Chem. Soc.*, 1973, 95: 4501), and ammonolysis as well as hydrazinolysis (Bodanszky, et al., *Chem. Ind.*, 1964, 32: 1423), hydrogenolysis (Jones, *Tetrahedron Lett.* 1977 18: 2853 and Schlatter, et al., *Tetrahedron Lett.* 1977 18: 2861), and photolysis (Rich and Gurwara, *J. Am. Chem. Soc.*, 1975 97: 1575).

Following deprotection and cleavage of the oligomer from the solid support, the oligomer is purified by any of several methods routinely used in the art. Suitable methods include HPLC and column chromatographic techniques, such as silica gel flash column chromatography.

Based on the recognition that most operations are identical in the synthetic cycles of solid-phase peptide synthesis, a new matrix, PEPS, was recently introduced (Berg, et al., *J.*

*Am. Chem. Soc.*, 1989, 111: 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple oligo-β-lactamamides, these being conceptually simple to synthesize since only four different reaction compartments are normally required, one for each of the four "pseudo-nucleotide" units.

Two other methods proposed for the simultaneous synthesis of large numbers of peptides may also apply to the preparation of multiple, different oligo-β-lactamamides. The first of these methods (Geysen, et al., *Proc. Natl. Acad. Sci. USA*, 1984, 81: 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, *Proc. Natl. Acad. Sci. USA*, 1985, 82: 5131) utilizes a "tea bag" containing traditionally-used polymer beads. Other relevant proposals for multiple peptide synthesis in the context of the present invention include the simultaneous use of two different supports with different densities (Tregear, in "*Chemistry and Biology of Peptides*", J. Meienhofer, ed., Ann Arbor Sci. Publ., Ann Arbor, 1972 pp. 175–178), combining of reaction vessels via a manifold (Gorman, *Anal. Biochem.*, 1984, 136: 397), multicolumn solid-phase synthesis (e.g. Krchnak, et al., *Int. J. Peptide Protein Res.*, 1989, 33: 209), and Holm and Meldal, in "*Proceedings of the 20th European Peptide Symposium*", G. Jung and E. Bayer, eds., Walter de Gruyter & Co., Berlin, 1989 pp. 208–210), and the use of cellulose paper (Eichler, et al., *Collect. Czech. Chem. Commun.*, 1989, 54: 1746).

While the conventional cross-linked styrene/divinylbenzene copolymer matrix and the PEPS support are expected to be very efficient in the context of the present invention for solid-phase synthesis, a non-limiting list of solid supports (polymer substrates) which will find use include: (1) Particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethytenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97: 6584, *Bioorg. Chem.* 1979, 8: 351), and J. C. S. Perkin I: 538 (1981)); (2) solid supports based on silica-containing particles such as porous glass beads and silica gel. One example is the reaction product of trichloro-[3-(4-chloromethyl)phenyl]propylsilane and porous glass beads (see Parr and Grohmann, *Angew. Chem. Internal.* Ed. 1972, 11: 314) sold under the trademark "PORASIL E" by Waters Associates, Framingham, Ma., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.*, 1970, 11: 4503); (3) solid supports which can be termed "composites" in that they contain two major ingredients: a resin and another material that is also substantially inert to the organic synthesis reaction conditions employed. One exemplary composite (see Scott, et al., *J. Chrom. Sci.*, 1971, 9: 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17: 243) and van Rietschoten in "Peptides 1974", Y. Wolman, Ed., Wiley and Sons, New York, 1975, pp. 113–116); and (4) contiguous solid supports other than PEPS, such as cotton sheets (Lebl and Eichler, *Peptide Res.* 1989, 2: 232) and hydroxypropylacrylate-coated polypropylene membranes (Daniels, et al., *Tetrahedron Lett.* 1989, 30: 4345).

Whether manually or automatically operated, solid-phase oligo-β-lactamamide synthesis in the context of the present invention may be performed batchwise. However, most of the syntheses may equally well be carried out in the continuous-flow mode, where the support is packed into columns (Bayer, et al., *Tetrahedron Lett.*, 1970, 2: 4503 and Scott, et al., *J. Chromatogr. Sci.*, 1971, 9: 577). With respect to continuous-flow solid-phase synthesis, the rigid poly (dimethyl-acrylamide)-Kieselguhr support (Atherton, et al., *J. Chem. Soc. Chem. Commun.*, 1981, 21: 1151) appears to be particularly successful, but another valuable configuration is the successfully applied to the standard copoly (styrene-1%-divinylbenzene) support (Krchnak, et al., *Tetrahedron Lett.*, 1987, 28: 4469).

While the solid-phase technique is presently preferred in the context of conventional synthesis of peptides and hence will be applicable to the present invention, other methodologies or combinations thereof, for example, in combination with the solid-phase technique, apply as well: (1) the classical solution-phase methods for peptide synthesis (e.g., Bodanszky, "*Principles of Peptide Synthesis*", Springer-Verlag, Berlin-New York 1984), either by stepwise assembly or by segment/fragment condensation, are of particular relevance when considering especially large scale productions (gram, and kilograms) of oligo β-lactamamide compounds; (2) the so-called "liquid-phase" strategy, which utilizes soluble polymeric supports such as linear polystyrene (Shemyakin, et al., *Tetrahedron Lett.*, 1965, 27: 2323) and polyethylene glycol (PEG) (Mutter and Bayer, *Angew. Chem., Int. Ed. Engl.*, 1974, 13: 88), is useful; (3) random polymerization (see, e.g., Odian, "*Principles of Polymerization*", McGraw-Hill, New York (1970)) yielding mixtures of many molecular weights ("polydisperse") peptide or oligo-β-lactamamides are particularly relevant for purposes such as screening for antiviral effects; (4) a technique based on the use of polymer-supported amino acid active esters (Fridkin, et al., *J. Am. Chem. Soc.*, 1965, 87:

4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, oligo-β-lactamamides, that can subsequently be used for fragment condensation into larger oligo-β-lactamamides; (5) oligo-β-lactamamides which may be assembled enzymatically by enzymes such as proteases or derivatives thereof with novel specificities (obtained, for example, by artificial means such as protein engineering), or via "oligo-β-lactamamide ligases" for the condensation of a number of oligo-β-lactamamide fragments into very large oligo-β-lactamamides; (6) via catalytic antibodies (abzymes), discovered simultaneously by the groups of Lerner (Tramantano, et al., *Science*, 1986, 234: 1566) and of Schultz (Pollack, et al., *Science*, 1986, 234, 1570), especially in view of recent success in producing abzymes catalyzing acyl-transfer reactions (see for example Shokat, et al., *Nature*, 1989, 338: 269) and references therein); oligo-β-lactamamide synthesis via artificial enzymes, pioneered by the Stewart group (Hahn, et al., *Science*, 1990, 248: 1544).

No single strategy may be wholly suitable for the synthesis of a specific oligo-β-lactamamide molecule, and for a particular application a combination of methods may produce optimal results. The choice of such methods which are most advantageous for a given application are within the ability of those possessing ordinary skill in the art.

Compounds of the invention also include chimetic oligomeric structures, which may be prepared by incorporation of non-β-lactamamide synthons into the β-lactamamide chain, using chemistries set forth above. Representative of such non-β-lactamamide synthons are monomeric amino acids, polypeptides and peptide nucleic acid monomeric and polymeric synthons.

Additional objects, advantages, and novel features of this invention will become apparent to those skilled in the art upon examination of the following examples thereof, which are not intended to be limiting.

Example 1

N-1-Carboxymethylthymine

To a suspension of thymine (0.317 mol) and potassium carbonate (0.634 mol) in dimethylformamide (900 ml) is added methyl bromoacetate (0.634 mol) and the mixture is stirred vigorously overnight under nitrogen. The mixture is filtered, washed with ether and evaporated to dryness, in vacuo, to afford a solid residue. The solid residue is treated with water (300 ml) and 4N hydrochloric acid (12 ml), stirred for 20 minutes at 0° C., filtered and washed with water (2×100 ml). The precipitate is treated with water and 2 N sodium hydroxide (60 ml), and is boiled for 10 minutes. The mixture is cooled at 0° C., filtered, and precipitated by the addition of 4N hydrochloric acid (70 ml) to afford the the pure title compound.

Example 2

N-Benzyloxycarbonyl-N-1-carboxymethyl Cytosine

To a suspension of N-benzyloxycarbonyl cytosine (0.317 mol) and potassium carbonate (0.317 mol) in dimethylformamide (900 ml) is added methyl bromoacetate (0.317 mol) and the mixture is stirred vigorously overnight under nitrogen. The mixture is filtered, washed with ether and evaporated to dryness, in vacuo. The solid residue is treated with water (300 ml) and 4N hydrochloric acid (12 ml), stirred for 20 minutes at 0° C., filtered and washed with water (2×100 ml). The precipitate is treated with water and 2N sodium hydroxide (60 ml), and is boiled for 10 minutes. The mixture is cooled to 0° C., filtered, and precipitated by the addition of 4N hydrochloric acid (70 ml) to afford the pure title compound.

Example 3

N-9-Carboxmethyladenine Methyl Ester

Adenine (74 mmoles) and potassium carbonate (74 mmoles) are suspended in DMF (100 ml) and methyl bromoacetate (74 mmoles) in DMF (20 ml) is added. The suspension is stirred for 3 hours under nitrogen at room temperature, and then filtered. The solid residue is washed three times with DMF (25 ml), and the combined filtrate is evaporated to dryness, in vacuo. The product obtained is poured into water and 4N hydrochloric acid is added to pH=6. After stirring for 20 minutes, the solid is filtered, washed with water and recrystallized from 95% ethanol to give the title compound.

Example 4

N-Benzyloxycarbonyl-N-9-carboxymethyl Adenine Methyl Ester

N-9-carboxymethyl adenine methyl ester (15 mmoles) is dissolved in DMF (50 ml) and added to a solution of N-ethyl-benzyloxycarbonylimidazole tetrafluoroborate (62 mmoles) in dichloromethane (50 ml) with ice-cooling. The ice-bath is removed and the reaction mixture is stirred over-night. The reaction mixture is treated with saturated sodium bicarbonate (100 ml). After stirring for 15 minutes, the two phases are separated and the organic phase is washed successively with water, potassium bisulfate, and brine. The solution is dried, concentrated and precipitated from petroleum ether to afford the title compound as solid.

Example 5

N-Benzyloxycarbonyl-N-9-carboxymethyl Adenine

A suspension of N-benzyloxycarbonyl-N-9-carboxymethyl adenine methyl ester (10 mmoles) is taken up in methanol (50 ml), cooled to 0° C., and 2N sodium hydroxide (50 ml) is added. The reaction mixture is stirred for 30 minutes and then acidified to pH 1.0 with 4N hydrochloric acid. The precipitate is filtered, washed with water and dried to give the title compound.

Example 6

N-(BOC) amino Acetonitrile

To a stirred suspension of aminoacetonitrile hydrochloride (0.1 mol) and triethyl amine (0.25 mol) in THF (150 ml) is added a solution of di-t-butyldicarbonate in THF (75 ml) at room temperature under argon. After stirring overnight, the reaction mixture is filtered and concentrated to give the title compound as an oil.

Example 7

N-(BOC)ethylenediamine

A solution of N-(BOC)amino acetonitrile (30 mmoles) in methanol (100 ml) is saturated with ammonia and hydrogenated using raney nickel on a Parr hydrogenator at 45 psi at room temperature for 10 hours. The reaction mixture is filtered, the catalyst washed with methanol (50 ml) and concentrated to give the title compound as an oil.

Example 8

Preparation of Imine

Methyl glyoxylate (40 mmoles) is dissolved in dichloromethane (150 ml), and a solution of N-(BOC)ethylenediamine (40 mmoles) in dichloromethane (50 ml) is added slowly under nitrogen at 0° C. The reaction mixture is stirred for 30 minutes and then 4A molecular sieves (15 g) are added to it. After stirring for 4 hours, the reaction mixture is filtered and concentrated to give the title compound as a viscous liquid.

Example 9

1-N-[N-(BOC)-2-aminoethyl]-3-(thymin-1-yl)-4-carbomethoxy-2-azetidinone

To a stirred suspension of N-1-carboxymethylthymine (20 mmoles) in DMF (50 ml) is added 2-chloro-1-methylpyridiniumiodide (20 mmoles). The mixture is heated gently till the solution becomes homogenous. The reaction mixture is slowly cooled to room temperature and then a solution of imine prepared in Example 8 (20 mmoles) in DMF (20 ml) is added slowly over a period of 20 minutes. The reaction mixture is stirred over-night and concentrated under vacuo. The crude product is purified by flash chromatography over silica gel to give the title compound as a solid.

Example 10

1-N-[N-(BOC)-2-aminoethyl]-3-(thymin-1-yl)-4-carboxyl-2-azetidinone

To a stirred solution of 1-N-[N-(BOC)-2-aminoethyl]-3-(thymin-1-yl)-4-carbomethoxy-2-azetidinone (10 mmoles) in methanol (50 ml) is added a 0.5N lithium hydroxide solution (10 ml). The mixture is stirred at room temperature for 10 hours. The reaction mixture is then cooled to 0° C. and acidified with 4N hydrochloric acid, concentrated and extracted with dichloromethane (3×25 ml). The organic phases are combined, washed with brine, dried and concentrated to afford the crude material. This material is purified by flash chromatography over silica gel to give the title compound as a solid.

Example 11

1-N-[N-(BOC)-2-aminoethyl]-3-(N-benzyloxycarbonyl-adenin-9-yl)-4-carbomethoxy-2-azetidinone To a stirred suspension of N-benzyloxycarbonyl-N-9-carboxymethyl adenine (20 mmoles) in DMF (50 ml) is added 2-chloro-1-methylpyridiniumiodide (20 mmoles). The mixture is heated gently till the solution becomes homogenous. The reaction mixture is slowly cooled to room temperature and then a solution of imine prepared in Example 8 (20 mmoles) in DMF (20 ml) is added slowly over a period of 20 minutes. The reaction mixture is stirred over-night and concentrated under vacuo. The crude product is purified by flash chromatography over silica gel to give the title compound as a solid.

Example 12

1-N-[N-(BOC)-2-aminoethyl]-3-(N-benzyloxycarbonyl-adenin-9-yl)-4-carboxyl-2-azetidinone To a stirred solution of 1-N-[N-(BOC)-2-aminoethyl]-3-(N-benzyloxycarbonyl-adenin-9-yl)-4-carbomethoxy-2-azetidinone (10 mmoles) in methanol (50 ml) is added a 0.5N lithium hydroxide solution (10 ml). The mixture is stirred at room temperature for 10 hours. The reaction mixture is then cooled to 0° C. and acidified with 4N hydrochloric acid. The mixture is concentrated and extracted with dichloromethane (3×25 ml). The organic phases are combined, washed with brine, dried and concentrated to afford the crude material. This material is purified by flash chromatography over silica gel to give the title compound as a solid.

Example 13

1-N-[N-(BOC)-2-aminoethyl]-3-(N-benzyloxycarbonyl-cytosin-1-yl)-4-carbomethoxy-2-azetidinone To a stirred suspension of N-benzyloxycarbonyl-N-1-carboxymethyl cytosine (20 mmoles) in DMF (50 ml) is added 2-chloro-1-methylpyridiniumiodide (20 mmoles). The mixture is heated gently till the solution becomes homogenous. The reaction mixture is slowly cooled to room temperature and then a solution of imine prepared in Example 8 (20 mmoles) in DMF (20 ml) is added slowly over a period of 20 minutes. The reaction mixture is stirred over-night and concentrated under vacuo. The crude product is purified by flash chromatography over silica gel to give the title compound as a solid.

Example 14

1-N-[N-(BOC)-2-aminoethyl]-3-(N-benzyloxycarbonyl-cytosin-1-yl)-4-carboxyl-2-azetidinone To a stirred solution of 1-N-[N-(BOC)-2-aminoethyl]-3-(N-benzyloxycarbonyl-cytosin-1-yl)-4-carboxyl-2-azetidinone (10 mmoles) in methanol (50 ml) is added a 0.5N lithium hydroxide solution (10 ml). The mixture is stirred at room temperature for 10 hours, cooled to 0° C., acidified with 4N hydrochloric acid, concentrated and extracted with dichloromethane (3×25 ml). The organic phases are combined, washed with brine, dried and concentrated to afford the crude material. This material is purified by flash chromatography over silica gel to give the title compound as a solid.

Example 15

1-N-[N-(BOC)-2-aminoethyl]-3-(N-benzyloxycarbonyl-guanosin-1-yl)-4-carbomethoxy-2-azetidinone To a stirred suspension of N-benzyloxycarbonyl cytosine (20 mmoles) in DMF (50 ml) is added 2-chloro-1-methylpyridiniumiodide (20 mmoles). The mixture is heated gently till the solution becomes homogenous. The reaction mixture is slowly cooled to room temperature and then a solution of imine prepared in Example 8 (20 mmoles) in DMF (20 ml) is added slowly over a period of 20 minutes. The reaction mixture is stirred overnight and concentrated under vacuo. The crude product is purified by flash chromatography over silica gel to give the title compound as a solid.

Example 16

1-N-[N-(BOC)-2-aminoethyl]-3-(N-benzyloxycarbonyl-guanosin-9-yl)-4-carboxyl-2-azetidinone To a stirred solution of 1-N-[N-(BOC)-2-aminoethyl]-3-(N-benzyloxycarbonyl-guanosin-9-yl)-4-carbomethoxy-2-azetidinone (10 mmoles) in methanol (50 ml) is added a 0.5N lithium hydroxide solution (10 ml). The mixture is stirred at room temperature for 10 hours. The reaction mixture is then cooled to 0° C. and acidified with 4N hydrochloric acid, concentrated and extracted with dichloromethane (3×25 ml). The organic phases are combined, washed with brine, dried and concentrated to afford the crude material. This material is purified by flash chromatography over silica gel to give the title compound as a solid.

Solution Phase Synthesis of an β-lactamamide Tetramer

Abbreviations:

A(bL)  1-N-[N-(BOC)-2-aminoethyl]-3-(N-benzyloxycarbonyl-N-adenin-9-yl)-4-carboxy-2-azetidinone C(bL)  1-N-[N-(BOC)-2-aminoethyl]-3-(N-benzyloxycarbonyl-N-cytosin-1-yl)-4-carboxy-2-azetidinone T(bL)  1-N-[N-(BOC)-2-aminoethyl]-3-(thymidin-1-yl)4-carboxy-2-azetidinone G(bL)  1-N-[N-(BOC)-2-aminoethyl]-3-(N-benzyloxycarbonyl-N-guanosin-9-yl)-4-carboxy-2-azetidinone

Example 17

Amide of T(bL)

The compound T(bL) (5 mmoles) is dissolved in methanol and cooled to 0° C. A stream of anhydrous ammonia is bubbled into the reaction mixture. After 1½ hours the ammonia is discontinued and the flask is sealed and allowed to warm to room temperature and stand overnight. The solvent is removed in vacuo and the residue recrystallized from ethyl acetate/hexane to give the title compound.

Example 18

Free Amine of the T(bL) Amide

The T(bL) amide from Example 17 (2 mmoles) is dissolved in a 1:1 (v:v) solution of dichloromethane and trifluoroacetic acid at 0° C. and allowed to stir for 1 hour. The solution is allowed to warm to room temperature and concentrated in vacuo. The residue is dissolved in chloroform and washed with saturated sodium bicarbonate and then brine. The organic solution is dried with magnesium sulfate and concentrated to give the title compound. The compound is coupled as isolated.

Example 19

Coupling T(bL) Free Amine with A(bL)

The free amine from Example 18 (2 mmoles) is dissolved in a 1:1 solution of DMF/Pyridine. The A(bL), (3 mmoles) is added in one portion followed by HBTU (2.7 mmoles) and diisopropyl ethyl amine (5 mmoles). This solution is stirred at room temperature for 2 hours. The progress of the reaction is monitored by TLC. When the reaction is complete, it is concentrated in vacuo and then dissolved in chloroform. The chloroform solution is washed with saturated sodium bicarbonate and brine solutions, dried over magnesium sulfate and concentrated to dryness. The residue is then flash chromatographed over silica gel to give the purified dimer.

Example 20

C(bL)-A(bL)-T(bL)-amide

The dimer prepared in Example 19 is treated with trifluoroacetic acid/dichloromethane as per the procedure of example 18. The free amine is then coupled to C(bL) (3 mmoles) using the procedure of Example 19 and purified by chromatography on silica gel.

Example 21

G(bn)-C(bL)-A(bL)-T(bL)-Amide

The trimer prepared in Example 20 is deprotected with trifluoroacetic acid and dichloromethane as per the procedure of example 18. The resulting free amine is then coupled with G(bL), (3 mmoles). The work-up and purification are carried out as per the procedure of example 19 to give the title tetramer.

Example 22

Gly-G(bL)-C(bL)-A(bL)-T(bL)-Amide (SEQ ID NO:1)

The BOC group on the G(bL) end of the tetramer prepared in Example 21 is removed with trifluoro-acetic acid and dichloromethane. The resulting free amine is coupled with BOC-glycine as per the procedure of Example 19. The resulting glycine-capped oligo β-lactamamide is chromatographed over silica gel and the terminal BOC group and protecting groups are removed using 10% trifluoromethane sulfonic acid in trifluoroacetic acid. The deprotected oligo β-lactamamide is isolated by concentrating the reaction mixture to an oil and precipitating the oligo β-lactamamide from ether followed by RP-HPLC for purification.

Solution Phase Synthesis of PNA-Trisubstituted β-lactam Chimeras

Abbreviations:

$^P$G  Guanosine PNA
$^P$A  Adenosine PNA
$^P$T  Thymidine PNA
$^P$C  Cytosine PNA

Example 23

Gly-$^P$G-$^P$C-A(bL)-$^P$T-amide (SEQ ID NO:2)

The amide of the BOC PNA T monomer is deprotected with trifluoro-acetic acid and dichloromethane as per the procedure of Example 18. To the free amine the A(bL) monomer is coupled using HBTU as per the procedure of Example 19 giving the A(bL)-$^P$T-amide dimer. The dimer is purified by chromatography. This dimer is then deprotected with trifluoroacetic acid and dichloromethane as per the procedure of Example 18. The PNA C monomer is then coupled with HBTU as per the procedure of Example 19 and the protected trimer is purified by chromatography. The amine is deprotected as per the procedure of Example 18 and the PNA G monomer is coupled with HBTU as per the procedure of Example 19. The coupled $^P$G group is deprotected with trifluoro-acetic acid and dichloromethane as per the procedure of Example 18. The free amine is capped with BOC-Glycine as per the procedure of Example 19. The tetramer is purified by chromatography and then deprotected using trifluoroacetic acid and 10% trifluoromethane sulfonic acid as per the procedure of Example 22. The deprotected compound is purified by RP-HPLC to give the title tetramer capped with a glycine.

Example 24

Gly-$^P$C-$^P$G-T(bL)-$^P$A-amide (SEQ ID NO:3)

The amide of the BOC PNA A monomer is deprotected with trifluoroacetic acid and dichloromethane as per the procedure of Example 18. The T(bL) monomer is coupled to the free amine using HBTU as per the procedure of Example 19 giving the T(bL)-$^P$A-amide dimer that is purified by chromatography. This dimer is then deprotected with trifluoroacetic acid and dichloromethane as per the procedure of Example 18. The PNA G monomer is then coupled with HBTU as per the procedure of Example 19 and the protected trimer is purified by chromatography. The amine is deprotected as per the procedure of Example 18 and the PNA C monomer is coupled with HBTU as per the procedure of Example 19. The coupled $^P$C group is deprotected with trifluoro-acetic acid and dichloromethane as per the procedure of Example 18. The free amine is capped with BOC-Glycine as per the procedure of Example 19. The tetramer is purified by chromatography and then deprotected using trifluoroacetic acid and 10% trifluoromethane sulfonic acid as per the procedure of Example 22. The deprotected compound is purified by RP-HPLC to give the title tetramer capped with glycine.

Example 25

Gly-$^P$G-C(bL)-$^P$A-$^P$T-amide (SEQ ID NO:4)

The amide of the BOC PNA T monomer is deprotected using trifluoroacetic acid and dichloromethane as per the procedure of Example 18. To this free amine is coupled the BOC PNA A monomer using HBTU as per the procedure of Example 19. Purification by silica gel chromatography followed by deprotection with trifluoroacetic acid as per the procedure of Example 18 and coupling with HBTU as per the procedure of Example 19 with the C(bL) monomer gives the protected trimer that is purified by chromatography. The trimer is deprotected with trifluoroacetic acid as per the procedure of Example 18 and the PNA G monomer is coupled with HBTU as per the procedure of Example 19. The coupled $^P$G group is deprotected with trifluoro-acetic acid and dichloromethane as per the procedure of Example 18. The free amine is capped with BOC-Glycine as per the procedure of Example 19. The fully protected tetramer is purified by chromatography and then deprotected with 10% trifluoromethane sulfonic acid in trifluoroacetic acid as per the procedure of Example 22. The deprotected compound is purified by RP-HPLC to give the title tetramer capped with glycine.

Example 26

Gly-$^P$C-G(bL)-$^P$A-$^P$T-amide (SEQ ID NO:5)

The amide of the BOC PNA T monomer is deprotected using trifluoroacetic acid and dichloromethane as per the procedure of Example 18. To this free amine is coupled the BOC PNA A monomer using HBTU as per the procedure of Example 19. Purification by chromatography using silica gel followed by deprotection with trifluoroacetic acid as per the procedure of Example 18 and coupling with HBTU as per the procedure of Example 19 with the G(bL) monomer gives the protected trimer that is purified by chromatography. The trimer is deprotected with trifluoroacetic acid as per the procedure of Example 18 and the PNA C monomer is coupled with HBTU as per the procedure of Example 19. The coupled $^P$G group is deprotected with trifluoro-acetic acid and dichloromethane as per the procedure of Example 18. The free amine is capped with BOC-Glycine as per the procedure of Example 19. The fully protected tetramer is purified by chromatography and then deprotected with 10% trifluoromethane sulfonic acid in trifluoroacetic acid as per the procedure of Example 22. The deprotected compound is purified by RP-HPLC to give the title tetramer capped with glycine.

Solid Phase Synthesis of an Oligo β-lactamamide Tetramer

Example 27

Gly-G(bL)-A(bL)-C(bL)-T(bL)-NH$_2$ (SEQ ID NO:6)

Methylbenzhydrylamine polystyrene support (50 mili equivalents) is placed in a solid-phase peptide synthesis vessel. N,N-dimethylformamide (3 ml) is added and the vessel is shaken for 20 minutes followed by draining of the solvent. To a vial are added 1-N-[N-(BOC)-2-aminoethyl]-3-thymin-1-yl-4-carbomethoxy-2-azetidinone (200 mmoles) and O-(benzotriazol-1-yl)-1,1,3,3-tetramethyluronium tetrafluoroborate (180 mmoles). N,N-Dimethylformamide (1 ml) and pyridine (1 ml) are added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. Any remaining free amine groups are capped by addition of a 10% solution of N-benzyloxycarbonyl-N'-methyl-imidazole triflate in N,N-dimethylformamide (1.5 ml). After shaking for five minutes, the capping solution is drained and the support washed five times with pyridine.

The support is washed four times with N,N-dimethylformamide/dichloromethane (1:1) and then treated twice with 5% m-cresol in trifluoroacetic acid (3 ml), with shaking for two minutes each time. The support is washed again with N,N-dimethylformamide/dichloromethane (1:1) and then with pyridine. To a vial are added 1-N-[N-(BOC)-2-aminoethyl]-3-(N-benzyloxycarbonyl-N-(cytosin-1-yl)-4-carbomethoxy-2-azetidinone (200 mmoles) and O-(benzotriazol-1-yl)-1,1,3,3-tetramethyluronium tetrafluoroborate (180 mmoles). N,N-Dimethylformamide (1 ml) and pyridine (1 ml) are added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 ml). After shaking for five minutes, the capping solution is drained and the support washed five times with pyridine.

The support is washed four times with N,N-dimethylformamide/dichloromethane (1:1) and then treated twice with 5% m-cresol in trifluoroacetic acid (3 ml) with shaking for two minutes each time. The support is washed again with N,N-dimethylformamide/dichloromethane (1:1) and then with pyridine. To a vial are added 1-N-[N-(BOC)-2-aminoethyl]-3-(N-benzyloxycarbonyl-N-adenin-9-yl)-4-carbomethoxy-2-azetidinone (200 mmoles) and O-(benzotriazol-1-yl)-1,1,3,3-tetramethyluronium tetrafluoroborate (180 mmoles). N,N-Dimethylformamide (1 ml) and pyridine (1 ml) are added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 ml). After shaking for five minutes, the capping solution is drained and the support washed five times with pyridine.

The support is washed four times with N,N-dimethylformamide/dichloromethane (1:1) and then treated twice with 5% m-cresol in trifluoroacetic acid (3 ml) with shaking for two minutes each time. The support is washed again with N,N-dimethylformamide/dichloromethane (1:1) and then with pyridine. To a vial are added 1-N-[N-(BOC)-2-aminoethyl]-3-(N-benzyloxycarbonyl-N-guanin-9-yl)-4-carbomethoxy-2-azetidinone (200 mmoles) and O-(benzotriazol-1-yl)-1,1,3,3-tetramethyluronium tetrafluoroborate (180 mmoles). N,N-Dimethylformamide (1 ml) and pyridine (1 ml) are added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 ml). After shaking for five minutes, the capping solution is drained and the support washed five times with pyridine.

The support is washed four times with N,N-dimethylformamide/dichloromethane (1:1) and then treated twice with 5% m-cresol in trifluoroacetic acid (3 ml) with shaking for two minutes each time. The support is washed again with N,N-dimethylformamide/dichloromethane (1:1) and then with pyridine. To a vial are added glycine (200 mmoles) and O-(benzotriazol-1-yl)-1,1,3,3-tetramethyluronium tetrafluoroborate (180 mmoles). N,N-Dimethylformamide (1 ml) and pyridine (1 ml) are added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. After washing with dichloromethane the support is dried under vacuum.

The dried support (350 mg) is placed in a solid-phase peptide synthesis vessel and washed twice for two minutes with trifluoroacetic acid. To the support are then added m-cresol (0.333 ml), dimethyl sulfide (1.0 ml), and trifluoroacetic acid (1.83 ml) and the flask is shaken for one minute. Trifluoromethanesulfonic acid (0.167 ml) is added dropwise with gentle shaking and the reaction is shaken for 1 hour. The solution is then drained off and the support is washed twice with trifluoroacetic acid and four times with diethyl ether. To the support are added m-cresol (0.417 ml) and trifluoroacetic acid (3.333 ml). Trifluoromethanesulfonic acid (0.417 ml) is added dropwise with gentle shaking and the reaction is shaken again for 1 hour. The reaction solution is then drained into a flask containing diethyl ether (100 ml) to precipitate the oligo β-lactamamide oligomer. The support is washed with trifluoroacetic acid (1.5 ml) and this solution is also drained into the diethyl ether solution. As much diethyl ether as possible is decanted from the precipitate which is then washed four times with additional diethyl ether (90 ml each wash). Residual diethyl ether is removed from the precipitate under vacuum. The oligo β-lactamamide oligomer is then purified by reverse phase HPLC.

Solid Phase Synthesis of PNA-Trisubstituted β-lactamamide Chimeric compounds

Example 28

Gly-$^P$G-$^P$A-C(bL)-$^P$T-NH$_2$ (SEQ ID NO:7)

The solid phase synthesis is performed as per the procedure of Example 27. The monomer used for the first coupling is 1-(BOC-aminoethylglycyl)thymine. For the second coupling 1-N-[N-(BOC)-2-aminoethyl]-3-(N-benzyloxycarbonyl-N-cytosin-1-yl)-4-carbomethoxy-2-azetidinone is used. N-Benzyloxycarbonyl-1-(BOC-aminoethylglycyl)adenine is the third monomer coupled to the resin bound material. The fourth coupling utilizes N-benzyloxycarbonyl-1-(BOC-aminoethylglycyl)guanine. Attachment of the terminal glycine, cleavage and purification are performed as above to give the tetramer.

Example 29

Gly-$^P$G-A(bL)-$^P$C-$^P$T-NH$_2$ (SEQ ID NO:8)

The solid phase synthesis is performed as per the procedure of Example 27. The monomer used for the first coupling is 1-(BOC-aminoethylglycyl)thymine. For the second coupling N-benzyloxycarbonyl-1-(BOC-aminoethylglycyl)cytosine is used. 1-N-[N-(BOC)-2-aminoethyl]-3-(N-Benzyloxycarbonyl-N-adenin-9-yl)-4-carbomethoxy-2-azetidinone is the third monomer coupled to the resin bound material. The fourth coupling utilizes N-benzyloxycarbonyl-1-(BOC-aminoethylglycyl)guanine. Attachment of the terminal glycine, cleavage and purification are performed as above to give the title tetramer.

Example 30

Gly-$^P$G-$^P$A-T(bL)-$^P$C-NH$^2$ (SEQ ID NO:9)

The solid phase synthesis is performed as per the procedure of Example 27. The monomer used for the first coupling is N-benzyloxycarbonyl-1-(BOC-aminoethylglycyl)-cytosine. For the second coupling 1-N-[N-(BOC)-2-aminoethyl]-3-thymidyl-4-carbomethoxy-2-azetidinone is used. N-Benzyloxycarbonyl-1-(BOC-aminoethylglycyl) adenine is the third monomer coupled to the resin bound material. The fourth coupling utilizes N-benzyloxycarbonyl-1-(BOC-aminoethylglycyl)-guanine. Attachment of the terminal glycine, cleavage and purification are performed as above to give the title tetramer.

Example 31

Gly-$^P$A-$^P$T-G(bL)-$^P$C-NH$_2$ (SEQ ID NO:10)

The solid phase synthesis is performed as per the procedure of Example 27. The monomer used for the first coupling is N-benzyloxycarbonyl-1-(BOC-aminoethylglycyl)-cytosine. For the second coupling 1-N-[N-(BOC)-2-aminoethyl]-3-(N-benzyloxycarbonyl-N-guanosin-9-yl)-4-carbomethoxy-2-azetidinone is used. 1-(BOC-aminoethylglycyl)thymine is the third monomer coupled to the resin bound material. The fourth coupling utilizes N-benzyloxycarbonyl-1-(BOC-amino-ethylglycyl)adenine. Attachment of the terminal glycine, cleavage and purification are performed as above to give the title tetramer.

EXAMPLE 32

Analysis of Double Strand Helix Formation Utilizing Circular Dichroism

The circular dichroism spectra of PNA-oligo β-lactamamide mixtures is obtained by titrating PNA having sequence Gly-GTAGATCACT (SEQ ID NO:11) with oligo β-lactamamide having sequence Gly-AGTGATCTAC (SEQ ID NO:12). The concentration of PNA is held constant (50 µmole/L) and the concentration of oligo β-lactamamide is increased to provide the following PNA-oligo β-lactamamide stoichiometrics: 0.25, 0.50, 0.75, 1.00, and 1.25. The hybridizations are performed in a 5 mmol/l sodium phosphate buffer, pH 7.0, at 20° C., after 20 minutes of incubation. The path length is 1 cm. Saturation is obtained at equimolar amounts of the two decamers.

The development of negative circular dichroism (at 220 nm) as a function of time, should be obtained after mixing equimolar amounts of PNA with oligo β-lactamamide. Samples are incubated at 5° C., 15° C., 23° C., 32° C., 41° C., and 47° C.

An Arrhenius plot is used to obtain rates from the CD kinetics. A plot provides the activation energy in kJ/mole (with the approximation that $(k_B T/h) \exp(\Delta S /R)$ is constant). The full rate equation is $k = (k_B T/h) \exp(-\Delta H) \exp(\Delta S /R)$ then gives $\Delta S$ in J/mole.

EXAMPLE 33

Oligo β-lactamamides Having Binding Affinity For The HIV-tat Protein As Measured in a Competitive Inhibition Assay Samples of oligo β-lactamamides corresponding to various TAR sequences prepared as per the above examples are incubated with recombinant tat transcription factor (100 µM) for 15 minutes at room temperature at 1, 3, 10, 30, and 100 µM (see, e.g., Cullen, et al., Cell 1990, 63, 655.). A competitor, a truncated version of the TAR sequence corresponding to residues 16–45 as a 2'-O-methyl oligonucleotide, is employed as a TAR sequence and is biotinylated at the 3'-O end by procedures generally in accordance with the protocols of application Ser. No. 08/032,852, Combinatorial Oligomer immunoabsorbant Screening Assay For Transcription Factors And Other Biomolecule Binding, filed Mar. 16, 1993, the entire contents of which are incorporated herein by reference. This TAR sequence is added at 100 nM concentration. The reaction is incubated for 20 minutes and then added to streptavidin-coated microtiter plate wells. After unbound molecules are washed away with phosphate-buffered saline (PBS), 100 µL of 1:500 tat antisera is added to each well and incubated for 2 hours. Protein A/G antisera phosphatase is bound to the tat antibodies and PNPP (p-nitrophenylphosphate) substrate (200 µl) is then added. Color development is measured 2 hours later by reading absorbance at 405 nM on a Titertek Multiscan ELISA plate reader.

EXAMPLE 34

Oligo β-lactamamide Having Binding Affinity For The C-myc Protein

C-myc is a nuclear protein involved in cell proliferation, differentiation, and neoplastic disease and binds DNA in a sequence specific manner. See, e.g., Nissen, Cancer Research 1986, 46, 6217 and Blackwell, Science 1990, 250, 1149. Crude nuclear extracts of c-myc are prepared generally in accordance with Franza, et al., Nature 1987, 330, 391, from HL 60 cells stimulated to induce the expression of c-myc.

Phosphorothioate oligonucleotides having the sequences GAT CCC CCC ACC ACG TGG TGC CTG A-B (SEQ ID NO:13, as a biotinylated phosphorothioate) and GAT CTC AGG CAC CAC GTG GTG GGG G-B (SEQ ID NO:14, as a biotinylated phosphorothioate), where B=biotin, are synthesized on an automated DNA synthesizer (Applied Biosystems model 380B) using modified standard phosphoramidite chemistry with oxidation by a 0.2M solution of 3H-1,2-benzodithiole-3-one 1,1-dioxide in acetonitrile for stepwise thiation of phosphite linkages. The thiation cycle wait step is 68 seconds and is followed by the capping step. β-Cyanoethyldiisopropyl phosphoramidites can be purchased from Applied Biosystems (Foster City, Calif.). Bases are deprotected by incubation in methanolic ammonia overnight. Following base deprotection, the oligonucleotides are dried in vacuo. Removal of 2'-hydroxyl t-butyldimethylsilyl protecting groups is effected by incubating the oligonucleotide in 1M tetra-butylammonium fluoride in tetrahydrofuran overnight. The RNA oligonucleotides are further purified on $C_{18}$ Sep-Pak cartridges (Waters, Division of Millipore Corp., Milford, Ma.) and ethanol precipitated. The phosphorothioate oligonucleotides are hybridized to create the double stranded NF-kB binding site.

A series of oligo β-lactamamide—oligo β-lactamamide duplexes is synthesized and hybridized to give a new series of oligo β-lactamamide duplexes corresponding to different length portions of the c-myc binding sequence. Each duplex is incubated in triplicate at concentrations of 1, 3, 10, 30, and 100 µM with the HL-60 extract described above. The myc P=S binding site is then added and the mixtures are incubated and washed with PBS. An antibody directed to the leucine zipper region of the myc protein (Santa Cruz Biotechnology) is added at a 1:1000 dilution. Non-bound molecules are washed away with PBS. Binding of myc to biotinylated c-myc transcription factor is quantitated by adding 100 µl of 1:500 tat antisera to each well for 2 hours. Protein A/G-alkaline phosphatase (Pierce; 1:5000; 100 µl) is then added and any excess is removed by washing with PBS. PNPP substrate (200 µl) is then added. Color development is measured 2 hours later by reading absorbance at 405 nM on a Titertek Multiscan ELISA plate reader.

EXAMPLE 35

Oligo β-lactamamide Having Binding Affinity For The C-rel Transcription Factor C-rel has been shown to represent a constituent of the NF-kB site binding transcription factor, which plays a crucial role in the expression of a number of genes including the immunoglobulin k light chain gene, IL-2ra, and MHC. (see, e.g., Gilmore, et al., Cell 1986, 62, 791.)

Crude nuclear extracts are prepared as detailed by Franza, et al., Nature 1987, 330, 391, from Jurkat cells stimulated 4 hours with 1 µM PHA and 100 nM PMA to induce the expression of rel. The extract is then preabsorbed with 100 µl streptavidin agarose per ml for 10 minutes. This is followed with the addition of poly dI.dC as a nonspecific competitor at a concentration of 100 µg/ml of extract. Nuclear extracts containing the biotinylated NF-kB binding site competitor are prepared as in Example 34, above.

A series of oligo β-lactamamide duplexes is synthesized to correspond to various length fragments of the consensus binding sequence of c-rel. NF-kB binding site competitor is added to each duplex and the resulting samples are washed. Antibody directed to rel is added. The amount of rel bound is quantitated by adding 100 µl of 1:500 rel antisera to each well for 2 hours. Protein A/G-alkaline phosphatase (Pierce; 1:5000; 100 µl) is then added and any excess is removed by washing with PBS. PNPP substrate (200 µl) is then added. Color development is measured 2 hours later by reading absorbance at 405 nM on a Titertek Multiscan ELISA plate reader.

EXAMPLE 36

Oligo β-lactamamide Having Binding Affinity For The AP-1 Transcription Factor

Genes belonging to the fos and jun oncogene families encode nuclear proteins associated with a number of transcriptional complexes, see, e.g., Konig, et al., *EMBO Journal* 1989, 8, 2559. C-jun is a major component of the AP-1 binding site, which was originally shown to regulate tissue plasminogen activator (TPA) induced expression of responsive genes through the TPA response element (TRE). The jun protein forms homo- or heterodimers which bind the TRE. The fos protein is only active as a heterodimer with any of the jun family of proteins. Fos/jun heterodimers have a much higher affinity for the TRE than jun homodimers.

Both the fos and the jun cDNA have been cloned downstream of the Sp6 promoter. RNA is produced from each plasmid in vitro, then used to produce functional jun and fos proteins in rabbit reticulocyte lystates. The fos and jun proteins are then allowed to bind to the biotinylated AP-1 binding site in competition with oligo β-lactamamide duplex sequences constructed as mimics of the proper consensus sequence for binding fos and jun, CGC TTG GTG ACT CAG CCG GAA (SEQ ID NO:15). Binding is quantitated with an antibody directed to fos or jun. When the fos alone is incubated with the AP-1 site there will be no detectable binding with either antibody. When the jun alone is incubated with the binding site, a signal will be detected with only the jun antibody. This is consistent with the formation of a jun homodimer, which has previously been demonstrated to bind AP-1. When the fos and jun proteins are mixed a signal will be detected with both fos and jun antibodies. This is consistent with the formation of a fos/jun homodimer which is known to bind the AP-1 site and should be detectable with either antibody.

Oligo β-lactamamide sequences of the present invention can be tested for the ability to block the formation of the fos/jun heterodimer. Molecules which block formation will decrease the signal detected with the fos antibody, but not the jun antibody.

EXAMPLE 37

Binding of Oligo β-lactamamides-$T_{10}/T_9C/T_8C_2$ to Double-Stranded DNA Targets $A_{10}/A_9G/A_8G_2$ A mixture of 200 cps $^{32}$P-labeled EcoRI-PvuII fragment (the large fragment labeled at the 3'-end of the EcoRI site) of the indicated plasmid, 0.5 µg carrier calf thymus DNA, and 300 ng oligo β-lactamamide in 100 µl buffer (200 mMNaCl, 50 mM Na-acetate, pH 4.5, 1 mM $ZnSO_4$) is incubated at 37° C. for 120 min. A 50 unit portion of nuclease $S_1$ is added and incubated at 20° C. for 5 min. The reaction is stopped by addition of 3 µl 0.5M EDTA and the DNA is precipitated by addition of 250 µl 2% potassium acetate in ethanol. The DNA is analyzed by electrophoresis in 10% polyacrylamide sequencing gels and the radiolabeled DNA bands visualized by autoradiography.

The target plasmids are prepared by cloning of the appropriate oligonucleotides into pUC19. Target $A_{10}$: oligonucleotides GATCCA$_{10}$G (SEQ ID NO:16) & GATCCT$_{10}$G (SEQ ID NO:17) cloned into the BamHI site (plasmid designated pT10). Target $A_5GA_4$: oligonucleotides TCGACT$_4$CT$_5$G (SEQ ID NO:18) & TCGACA$_5$GA$_4$G (SEQ ID NO:19) cloned into the SalI site (plasmid pT9C). Target $A_2GA_2GA_4$: oligonucleotides CA$_2$GA$_2$GA$_4$CTGCA (SEQ ID NO:20) and GT$_4$CT$_2$CT$_2$CTGCA (SEQ ID NO:21) into the PstI site (plasmid pTSC2). The sequence is read off of the gel.

EXAMPLE 38

Inhibition of Restriction Enzyme Cleavage by Oligo β-lactamamide

A 2 µg portion of plasmid pT10 is mixed with the indicated amount of oligo β-lactamamide $T_{10}$ (SEQ ID NO:22) in 20 µl TE buffer (10 mM Tris-HCl, mM EDTA, pH 7.4) and incubated at 37° C. for 120 min. 2 µl 10×buffer (10 mM Tris-HCl, pH 7.5, 10 mM, $MgCl_2$, 50 mM NaCl, 1 mM DTT). PvuII (2 units) and BamHI (2 units) are added and the incubation is continued for 60 min. The DNA is analyzed by gel electrophoresis in 5% polyacrylamide and the DNA is visualized by ethidium bromide staining.

EXAMPLE 39

Kinetics of Oligo β-lactamamide-$T_{10}$—dsDNA Strand Displacement Complex Formation A mixture of 200 cps $^{32}$P-labeled EcoRI-PvuII fragment of pT10 (the large fragment labeled at the 3'-end of the EcoRI site), 0.5 µg carrier calf thymus DNA, and 300 ng of oligo β-lactamamide Gly-$T_{10}$ (SEQ ID NO:22) in 100 µl buffer (200 mM NaCl, 50 mM Na-acetate, pH 4.5, 1 mM $ZnSO_4$) are incubated at 37° C. 50 U of $S_1$ nuclease is added to each of 7 samples and incubation is continued for 5 min at 20° C. The DNA is then precipitated by addition of 250 µl 2% K-acetate in ethanol and analyzed by electrophoresis in a 10% polyacrylamide sequencing gel. The amount of strand displacement complex is calculated from the intensity of the $S_1$-cleavage at the target sequence, as measured by densitometric scanning of autoradiographs.

EXAMPLE 40

Stability of oligo β-lactamamide-dsDNA Complexes

A mixture of 200 cps $^{32}$P-pT10 fragment, 0.5 µg calf thymus DNA and 300 ng of the desired oligo β-lactamamide, (either Gly-$T_{10}$ (SEQ ID NO:22), Gly-$T_8$ (SEQ ID NO:23) or Gly-$T_6$ (SEQ ID NO:24) is incubated in 100 µl 200 mM NaCl, 50 mM Na-acetate, pH 4.5, 1 mM $ZnSO_4$ for 60 min at 37° C. A 2 µg portion of oligonucleotide GATCCA$_{10}$G (SEQ ID NO:25) is added and each sample is heated for 10 min, cooled in ice for 10 min and warmed to 20° C. A 50 U portion of $S_1$ nuclease is added and the samples are analyzed and quantified.

EXAMPLE 41

Biological stability of Oligo β-lactamamides

A mixture of oligo β-lactamamide Gly-$T_5$ (SEQ ID NO:26) (10 µg) and a control, "normal" peptide (10 µg) in 40 µl 50 mM Tris-HCl, pH 7.4 is treated with varying amounts of peptidase from porcine intestinal mucosa or protease from *Streptomyces caespitosus* for 10 min at 37° C. The amount of oligo β-lactamamide and peptide is determined by HPLC analysis (reverse phase C-18 column: 0–60% acetonitrile, 0.1% trifluoroacetic acid).

EXAMPLE 42

Inhibition of Gene Expression

A preferred assay to test the ability of oligo β-lactamamides to inhibit expression of the E2 mRNA of papilloma-virus is based on the well-documented transactivation properties of E2. Spalholtz, et al., *J. Virol.*, 1987, 61, 2128–2137. A reporter plasmid (E2RECAT) is constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of oligo β-lactamamides to the growth medium at final concentrations of 5, 15 and 30 mM. The next day cells are transfected with 10 µg of E2RE1CAT by calcium phosphate precipitation. Ten micrograms of E2RE1CAT and 10 µg of carrier DNA (PUC 19) are mixed with 62 µl of 2M $CaCl_2$ in a final volume of 250 µl of $H_2O$, followed by addition of 250 µl of 2× HBSP (1.5 mM $Na_2PO_2$, 10 mM KCl, 280 mMNaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 mM $Na_2PO_2$, 5 mM KCl, 140 mM NaCl, 6 mM glucose and 25 mM HEPES, pH 7.0. After shocking, cells are washed 2 times with serum free DMEM and fed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 µl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 µl of cell extract, 5 µl of 4 mM acetyl coenzyme A, 18 µl $H_2O$ and 1 µl $^{14}C$-chloramphenicol, 40–60 mCi/mM. After incubation, chloramphenicol (acetylated and nonacetylated forms) is extracted with ethyl acetate and evaporated to dryness. Samples are resuspended in 25 µl of ethyl acetate, spotted onto a TLC plate and chromatographed in chloroform-:methanol (19:1). Chromatographs are analyzed by autoradiography. Spots corresponding to acetylated and nonacetylated $^{14}C$-chloramphenicol are excised from the TLC plate and counted by liquid scintillation for quantitation of CAT activity. Oligo β-lactamamides that depress CAT activity in a dose dependent fashion are considered positives.

B. Inhibition of HPV E2 Expression

The assay for inhibition of human papillomavirus (HPV) E2 by oligo β-lactamamides is essentially the same as that for BPV-1 E2. For HPV assays appropriate HPVs are co-transfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for antisense studies. For each oligo β-lactamamide, cells are pretreated as above, transfected with E2RE1CAT, and analyzed for CAT activity as above. Oligo β-lactamamides are considered to have a positive effect if they can depress CAT activity in a dose dependent fashion.

EXAMPLE 43

Triplexing of oligo β-lactamamides to nucleic acids—Probing protocols

Probing is effected in 100µ buffer (S1: 100 mM NaCl, 1 mM $ZnSO_4$, 50 mM NaAc, pH 4.5; $KMnO_4$/dimethyl sulphate (DMS): 10 mM Na-cacodylate, 1 mM EDTA, pH 7.0) containing about 200 cps $^{32}P$-labeled DNA fragment, 0.5 µg calf thymus DNA and the desired amount of oligo β-lactamamide. Following a preincubation for 60 min at 37° C., the probing reagent is added and the incubation is continued at room temperature. The reactions are terminated by the addition of a stop-buffer. The DNA is precipitated by addition of 200 µL 2% KAc in 96% EtOH and is analyzed by electrophoresis in 10% polyacrylamide sequencing gels. Radioactive DNA bands are visualized by autoradiography using amplifying screens and Agfa curix RPA X-ray films exposed at—70° C.

Probing conditions are: S1: 0.5 U/µl, 5 min. stopped with 3 µl 1M EDTA; $KMnO_4$: 1 mM, 15 sec. stopped with 50 µl 1M 6-mercaptoethanol, 1.5M NaAc, pH 7.0; DMS: 1% DMS, 15 sec., stopped as for $KMnO_4$ probing. Samples probed with DMS or $KMnO_4$ are treated with piperidine (0.5M, 90° C., 20 min.) prior to gel analysis.

EXAMPLE 44

Chemical probing of the binding of Oligo β-lactamamide Gly-$T_2CT_2CT_4$ (SEQ ID NO:28) to pA8G2

For this example, the 248 bp EcoRI/PvuII fragment of pASG2 is $^{32}P$-end-labeled at either the 5' or the 3' at the EcoRI site. Probing is effected as per the protocols of Example 43. A control is run in S1 buffer without $S_1$ nuclease and without oligo β-lactamamide. Probing is effected on 8 samples, 4 using $KMnO_4$ and 4 other samples using DMS. The following concentrations of oligo β-lactamamide are used: 0 µM, 0.25 µM, 2.5 µM or 25 µM.

In order to assure that the results are not an artifact of the dimeric target, another experiment is performed using a plasmid (pASG2) having only a single oligo β-lactamamide target. The target is probed with KMnO$_4$ and DMS.

Probing is effected in 100μ buffer (S1: 100 mM NaCl, 1 mM ZnSO$_4$, 50 mM NaAc, pH 4.5; KMnO$_4$/dimethyl sulphate (DMS): 10 mM Na-cacodylate, 1 mM EDTA, pH 7.0 or as other wise noted) containing about 200 cps $^{32}$P-labeled plasmid (pASG2) and the desired amount of oligo β-lactamamide. Following a preincubation for 60 min at 37° C., the probing reagent is added and the incubation is continued at room temperature. The reactions are terminated by the addition of a stop-buffer. The DNA is precipitated by addition of 200 μL of 2% KAc in 96% EtOH and is analyzed by electrophoresis in 10% polyacrylamide sequencing gels. Radioactive DNA bands are visualized by autoradiography-using amplifying screens and Agfa curix RPA X-ray films exposed at −70° C.

EXAMPLE 45

Unwinding of closed circular DNA with Oligo β-lactamamide

Relaxed circular DNA is prepared by treating ordinary supercoiled plasmid DNA with an extract containing DNA topoisomerase I, as described by V. I. Lyamichev, et. al., *J. Biomolec. Struct. Dynamics*, 3, 327–338 (1985). DNA-oligo β-lactamamide complexes are obtained by incubation of 1–2 μg of DNA in 5–20 μL TE with 0.4 optical units/mL of oligo β-lactam-amide for 4 hours at 20°–22° C. This corresponds to about a 10 time molar excess of oligo β-lactamamide to its potential binding sites. Agarose (1.5%) gel electrophoresis is performed in a TAE buffer containing 1 μg/mL of chloroquine at 10° C. for 15 hours at 1.5 V/cm. Two-dimensional gel electrophoresis is preformed in the first direction (from top to bottom) in the TAE buffer and in the second direction (from left to right) in the same buffer with addition of 1 μg/mL of chloroquine.

In this example, the efficiency of oligo β-lactamamide Gly-T10 (SEQ ID NO:22) incorporating into the DNA duplex and displacing the DNA T-strand in solution is shown by unwinding of closed circular DNA by oligo β-lactamamide. The pA98 plasmid is prepared in the form of relaxed circles (rcDNA). It is expected that complexing with oligo β-lactamamide would unwind about 10 turns of the DNA duplex. Because of topological constraints (the two strands in rcDNA are closed and therefore topologically linked), this unwinding would make the rcDNA molecules behave as if they were positively supercoiled by 10 superturns. This would manifest itself in an increase of electrophoretic mobility of the complex as compared with control rcDNA preincubated in the same buffer without oligo β-lactamamide.

EXAMPLE 46

Inhibition of RNA polymerase T$_3$ transcription elongation by oligo β-lactamamide The complex between oligo β-lactamamide Gly-T$_{10}$ (SEQ ID NO:22) (1 or 10 uM) and pAIOKS (pBluescriptKS$^+$in which the d(A$_{10}$) target is cloned into the BamH1 site, analogous to pT10) (100 ng) cleaved with restriction enzyme PvuII, XbaI, or BamH1, is formed by incubation in 14 μL of 10 mM Tris-HCl, 1 mM EDTA, (pH 7.4) buffer for 60 min. at 37° C. Subsequently 4 μL of 5× concentrated polymerase buffer (0.2M Tris-HCl, pH 8.0, 125 mM NaCl, 40 mM MgCl$_2$, 10 mM spermidine) is added together with 15 U T$_3$ RNA polymerase and ATP (10 mM), CTP (10 mM), GTP (10 mM), UTP (1 mM) and $^{32}$P-UTP (0.1 μCi), and the incubation is continued for 10 min. Following ethanol precipitation, the RNA is analyzed by electrophoresis in sequencing gels and the radiolabeled bands are visualized by autoradiography using intensifying screens.

EXAMPLE 47

Inhibition of Tag DNA polymerase primer extension by oligo β-lactamamide

A mixture of 100 ng PvuII cleaved plasmid pAIOKS, 0.1 ug M13 reverse primer and 1 ug of oligo β-lactamamide Gly-T$_{10}$ (SEQ ID NO:22) in 10 ul buffer (10 mM Tris-HCl, pH 8.3, 50 mM KCl, 1.5 mM MgCl$_2$, 0.1 mg/ml gelatine) is incubated for 5 min at 90° C. and then for 60 min at 37° C. Subsequently, 1 U of Taq polymerase, 1 ul dCTP (100 uM), dGTP (100 uM), dTTP (100 uM) and $^{32}$P-dATP (1 uCi) are added and the incubation continued for 5 min at 20° C. Following the addition of 2 ul dATP, dCTP, dGTP, dTTP (1 mM each), the sample is incubated for 15 min at 60° C. The DNA is precipitated with ethanol and the samples treated as described for Example 46.

EXAMPLE 48

Inhibition of transcription by Oligo β-lactamamide

The oligo β-lactamamides Gly-T$_{10}$ (SEQ ID NO:22), Gly-T$_5$CT$_4$ (SEQ ID NO:27) and Gly-T$_2$CT$_2$CT$_4$ (SEQ ID NO:28) are synthesized as per the procedures of the above examples. Plasmids containing the target sequences are obtained by cloning of the appropriate oligonucleotides into the vector pBluescripKS$^+$. To obtain pT10KS and pA10KS, 16-mers 5'-TCGACT$_4$CT$_5$G (SEQ ID NO:18) and 5'-GATCCA$_{10}$G (SEQ ID NO:16) are cloned into the BamH1 site, and clones containing the insert in either orientation are isolated. pT9CA9GKS is obtained by cloning 5'-TCGACT$_4$CT$_5$G (SEQ ID NO:18) and 5'-TCGACA$_5$GA$_4$G (SEQ ID NO:19) into the SalI site and pT8C2KS and pA8G2KS are obtained by cloning 5'-GT$_4$CT$_2$CT$_2$CTGCA (SEQ ID NO:21) AND 5'-GA$_2$GA$_2$GA$_4$CTGCA (SEQ ID NO:20) into the PstI site. *E. coli* JM103 is used as host in all cases, and transformations and isolation of clones are done by standard techniques. Plasmids are purified by buoyant density centrifugation in CsCl gradients and characterized by dideoxy sequencing.

Inhibition of RNA polymerase transcription elongation by Oligo β-lactamamide

The complex between the desired oligo β-lactamamide and the desired DNA (100 ng) cleaved with the desired restriction enzyme is formed by incubation in 14 μL 10 mM Tris-HCl, 1 mM EDTA, (pH 7.4) buffer for 60 min at 37° C. Subsequently 4 μL 5× concentrated polymerase buffer (0.2M Tris-HCl, pH 8.0, 125 mM NaCl, 40 mM MgCl$_2$, 10 mM spermidine) is added together with 15 U of RNA polymerase and ATP (10 mM), CTP (10 mM), UTP (1 mM) and $^{32}$P-UTP (0.1 μCi). The incubation is continued for 10 min. Following ethanol precipitation, the RNA is analyzed by electrophoresis in polyacrylamide sequencing gels, and radiolabeled RNA bands are visualized by autoradiography (using Agfa Curix RPI X-ray films and intensifying screens). Quantitation is performed by densitometric scanning using a Molecular Dynamics laser scanner and the ImageQuant™ software.

EXAMPLE 49

RNA polymerase footprinting

DNase I footprinting experiments are undertaken to define where on the DNA fragment binding takes place. DNA fragments are labeled in the 3' end with klenow polymerase and $^{32}$P-dXTP. The oligo β-lactamamide-DNA complexes are formed by combining 0.3µ, oligo β-lactamamide (50 OD) with DNA fragments in 10 mM Tris-HCl pH 8.0 and 0.1 mM EDTA in a total volume of 25 µL for 1 hour at 37° C. The RNA Polymerase-oligo β-lactamamide/DNA complexes are formed by addition of 50–100 mM E. coli RNA Polymerase holoenzyme, T3 and T7. The reaction mix contains a final concentration of: 40 mM Tris-HCl pH 8.0, 120 mM KCl, 5 mM MgCl$_2$, 0.1 mM DTT and 1 mM of ATP, CTP, GTP and 0,1, mM of UTP and $^{32}$P UTP plus 2 ug/ml calf Thymus DNA in a total volume of 100 ul.

After 15 min. incubation at 37° C. the samples are digested with 0.03 µL DNAse (1 mg/ml) for 3 min followed by ethanol precipitation and analyzing by 8% denaturing PAGE.

EXAMPLE 50

Gel-Shift assay

The oligo β-lactamamide-DNA complexes are formed as per the footprint experiment in Example 49. After 15 min at 37° C. incubation the samples are analyzed on 5% PAGE. The gel-shift and DNaseI footprinting results are expected to demonstrate E. coli RNA polymerase binding to an oligo β-lactamamide/dsDNA strand displacement loop. The binding is expected to differ distinctly from that seen for RNA polymerase in the initiation and in the elongation complex. Binding of the oligo β-lactamamide/DNA complex likely will be confined to the DNA loop and will not extend significantly into the surrounding double-stranded DNA.

Although the (oligo β-lactamamide)=/DNA, DNA triplex-D-loop structurally does resemble an RNA transcription elongation loop, it differs in one important aspect; the oligo β-lactamamide does not contain a 3'-hydroxyl group to be used as an elongation substrate for RNA polymerase. The length of the resulting transcript is expected to correspond to a run-off transcript initiated at the bound oligo β-lactamamide. The transcription should be more efficient if a double oligo β-lactamamide target is used, giving rise to a loop of approximately 30 bases in the cis configuration, and approximately 16 bases in the trans configuration. In the latter case, transcripts of two distinct sizes should be produced which in length corresponds to initiation at both oligo β-lactamamide targets and proceeding in opposite directions.

Two experiments are undertaken to estimate the strength of the oligo β-lactamamide dependent transcription initiation. In one experiment, both the oligo β-lactamamide target and the strong CAP independent UV5 promoter are present on the same DNA fragment. Upon titration with oligo β-lactamamide the full run-off transcript from the UV5 promoter is inhibited, while a new transcript corresponding to transcription arrest at the oligo β-lactamamide site appears. However, when a DNA fragment containing a triple oligo β-lactamamide binding site is used, transcription from this "oligo β-lactamamide-promoter" is expected to be able to compete fully with the UV5 promoter. As the oligo β-lactamamide concentration is increased, transcription from the UV5 promoter will decrease with concomitant increases in the amounts of two transcripts that correspond in length to the products expected for transcription in either from the "oligo β-lactamamide-promoter". An analogous experiment is performed in trans using a mixture of a UV5 containing DNA fragment and either of the DNA fragments containing the single or the cis or trans double oligo β-lactamamide targets. The results of these experiments will confirm that a single oligo β-lactamamide decamer target is not able to compete with the UV5 promoter, whereas both of the dimeric targets compete very efficiently. While we do not want to be bound by theory, the results should suggest that a single-stranded DNA loop is a major structural determinant for RNA polymerase upon transcription initiation and elongation.

---

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 5
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 2
        ( D ) OTHER INFORMATION: /label=MODIFIED-SITE
           / note="Heterocyclic base guanine is attached to 1-
           N- [N- (BOC-)-2-aminoethyl]-4-
           carboxy-2- azetidinone through the C-3 group at
           position 9 of the base."

( i x ) FEATURE:
        ( A ) NAME/KEY: Modified-site (B) LOCATION: 3
(D) OTHER INFORMATION: /label=MODIFIED-SITE
/ note="Heterocyclic base cytosine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 4
(D) OTHER INFORMATION: /label=MODIFIED-SITE
/ note="Heterocyclic base adenine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 5
(D) OTHER INFORMATION: /label=MODIFIED-SITE
/ note="Heterocyclic base thymine is attached to 1-
N-[N-(BOC)- 2-aminoethyl]-4-carboxy-2-azetidinone
through the C-3 group at position 1 of the base."

(xi) SEQUENCE DESCRIPTION: SEQ ID NO:1:

```
Gly  Xaa  Xaa  Xaa  Xaa
1                   5
```

(2) INFORMATION FOR SEQ ID NO:2:

(i) SEQUENCE CHARACTERISTICS:
(A) LENGTH: 5
(B) TYPE: amino acid
(C) STRANDEDNESS: single
(D) TOPOLOGY: unknown (ii) MOLECULE TYPE: peptide (ix) FEATURE:
(A) NAME/KEY: Modified-site
(B) LOCATION: 2
(D) OTHER INFORMATION: /label=MODIFIED-SITE
/ note="Heterocyclic base guanine is attached to N-
acetyl (2- aminoethyl)glycine through the N-
acetyl group at position 9 of the base."

(ix) FEATURE:
(A) NAME/KEY: Modified-site
(B) LOCATION: 3
(D) OTHER INFORMATION: /label=MODIFIED-SITE
/ note="Heterocyclic base cytosine is attached to N-
acetyl (2- aminoethyl)glycine through the N-acetyl
group at position 1 of the base."

(ix) FEATURE:
(A) NAME/KEY: Modified-site
(B) LOCATION: 4
(D) OTHER INFORMATION: /label=MODIFIED-SITE
/ note="Heterocyclic base adenine is attached to 1-
N-[N-(BOC)- 2-aminoethyl]-4-carboxy-2-azatidinone
through the C-3 group at position 9 of the base."

(ix) FEATURE:
(A) NAME/KEY: Modified-site
(B) LOCATION: 5
(D) OTHER INFORMATION: /label=MODIFIED-SITE
/ note="Heterocyclic base thymine is attached to N-
acetyl (2- amidoethyl)glycine through the N-acetyl
group at position 1 of the base."

(xi) SEQUENCE DESCRIPTION: SEQ ID NO:2:

```
Gly  Xaa  Xaa  Xaa  Xaa
1                   5
```

(2) INFORMATION FOR SEQ ID NO:3:

(i) SEQUENCE CHARACTERISTICS:
(A) LENGTH: 5

(B) TYPE: amino acid
(C) STRANDEDNESS: single
(D) TOPOLOGY: unknown (ii) MOLECULE TYPE: peptide (ix) FEATURE:
    (A) NAME/KEY: Modified-site
    (B) LOCATION: 2
    (D) OTHER INFORMATION: /label=MODIFIED-SITE
        /note="Heterocyclic base cytosine is attached to N-acetyl (2- aminoethyl)glycine through the N-acetyl group at position 1 of the base."

(ix) FEATURE:
    (A) NAME/KEY: Modified-site
    (B) LOCATION: 3
    (D) OTHER INFORMATION: /label=MODIFIED-SITE
        /note="Heterocyclic base guanine is attached to N-acetyl (2- aminoethyl)glycine through the N-acetyl group at position 9 of the base."

(ix) FEATURE:
    (A) NAME/KEY: Modified-site
    (B) LOCATION: 4
    (D) OTHER INFORMATION: /label=MODIFIED-SITE
        /note="Heterocyclic base thymine is attached to 1-N-[N-(BOC)- 2-aminoethyl]-4-carboxy-2-azetidinone through the C-3 group at position 1 of the base."

(ix) FEATURE:
    (A) NAME/KEY: Modified-site
    (B) LOCATION: 5
    (D) OTHER INFORMATION: /label=MODIFIED-SITE
        /note="Heterocyclic base adenine is attached to N-acetyl (2- amidoethyl)glycine through the N-acetyl group at position 9 of the base."

(xi) SEQUENCE DESCRIPTION: SEQ ID NO:3:

Gly Xaa Xaa Xaa Xaa
1                       5

(2) INFORMATION FOR SEQ ID NO:4:

(i) SEQUENCE CHARACTERISTICS:
    (A) LENGTH: 5
    (B) TYPE: amino acid
    (C) STRANDEDNESS: single
    (D) TOPOLOGY: unknown (ii) MOLECULE TYPE: peptide (ix) FEATURE:
    (A) NAME/KEY: Modified-site
    (B) LOCATION: 2
    (D) OTHER INFORMATION: /label=MODIFIED-SITE
        /note="Heterocyclic base guanine is attached to N-acetyl (2- aminoethyl)glycine through the N-acetyl group at position 9 of the base."

(ix) FEATURE:
    (A) NAME/KEY: Modified-site
    (B) LOCATION: 3
    (D) OTHER INFORMATION: /label=MODIFIED-SITE
        /note="Heterocyclic base cytosine is attached to 1-N-[N-(BOC)- 2-aminoethyl]-4-carboxy-2-azetidinone through the C-3 group at position 1 of the base."

(ix) FEATURE:
    (A) NAME/KEY: Modified-site
    (B) LOCATION: 4
    (D) OTHER INFORMATION: /label=MODIFIED-SITE
        /note="Heterocyclic base adenine is attached to N-acetyl (2- aminoethyl)glycine through the N-acetyl group at position 9 of the base."

(ix) FEATURE:
    (A) NAME/KEY: Modified-site (B) LOCATION: 5
(D) OTHER INFORMATION: /label=MODIFIED-SITE
/ note="Heterocyclic base thymine is attached to N-acetyl (2- amidoethyl)glycine through the N-acetyl group at position 1 of the base."

(x i) SEQUENCE DESCRIPTION: SEQ ID NO:4:

Gly Xaa Xaa Xaa Xaa
1               5

(2) INFORMATION FOR SEQ ID NO:5:

(i) SEQUENCE CHARACTERISTICS:
(A) LENGTH: 5
(B) TYPE: amino acid
(C) STRANDEDNESS: single
(D) TOPOLOGY: unknown (i i) MOLECULE TYPE: peptide (i x) FEATURE:
(A) NAME/KEY: Modified-site
(B) LOCATION: 2
(D) OTHER INFORMATION: /label=MODIFIED-SITE
/ note="Heterocyclic base cytosine is attached to N-acetyl (2- aminoethyl)glycine through the N-acetyl group at position 1 of the base."

(i x) FEATURE:
(A) NAME/KEY: Modified-site
(B) LOCATION: 3
(D) OTHER INFORMATION: /label=MODIFIED-SITE
/ note="Heterocyclic base guanine is attached to 1-N-[N-(BOC)- 2-aminoethyl]-4-carboxy-2-azetidinone through the C-3 group at position 9 of the base."

(i x) FEATURE:
(A) NAME/KEY: Modified-site
(B) LOCATION: 4
(D) OTHER INFORMATION: /label=MODIFIED-SITE
/ note="Heterocyclic base adenine is attached to N-acetyl (2- aminoethyl)glycine through the N-acetyl group at position 9 of the base."

(i x) FEATURE:
(A) NAME/KEY: Modified-site
(B) LOCATION: 5
(D) OTHER INFORMATION: /label=MODIFIED-SITE
/ note="Heterocyclic base thymine is attached to N-acetyl (2- amidoethyl)glycine through the N-acetyl group at position 1 of the base."

(x i) SEQUENCE DESCRIPTION: SEQ ID NO:5:

Gly Xaa Xaa Xaa Xaa
1               5

(2) INFORMATION FOR SEQ ID NO:6:

(i) SEQUENCE CHARACTERISTICS:
(A) LENGTH: 5
(B) TYPE: amino acid
(C) STRANDEDNESS: single
(D) TOPOLOGY: unknown (i i) MOLECULE TYPE: peptide (i x) FEATURE:
(A) NAME/KEY: Modified-site
(B) LOCATION: 2
(D) OTHER INFORMATION: /label=MODIFIED-SITE
/ note="Heterocyclic base guanine is attached to 1-N-[N-(BOC)- 2-aminoethyl]-4-carboxy-2-azetidinone through the C-3 group at position 9 of the base."

(i x) FEATURE:
(A) NAME/KEY: Modified-site (B) LOCATION: 3
(D) OTHER INFORMATION: /label=MODIFIED-SITE
/ note="Heterocyclic base adenine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 4
(D) OTHER INFORMATION: /label=MODIFIED-SITE
/ note="Heterocyclic base cytosine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 5
(D) OTHER INFORMATION: /label=MODIFIED-SITE
/ note="Heterocyclic base thymine is attached to 1-
N-[N-(BOC)- 2-amidoethyl]-4-carboxy-2-azetidinone
through the C-3 group at position 1 of the base."

(xi) SEQUENCE DESCRIPTION: SEQ ID NO:6:

Gly  Xaa  Xaa  Xaa  Xaa
1                    5

(2) INFORMATION FOR SEQ ID NO:7:

(i) SEQUENCE CHARACTERISTICS:
(A) LENGTH: 5
(B) TYPE: amino acid
(C) STRANDEDNESS: single
(D) TOPOLOGY: unknown (ii) MOLECULE TYPE: peptide (ix) FEATURE:
(A) NAME/KEY: Modified-site
(B) LOCATION: 2
(D) OTHER INFORMATION: /label=MODIFIED-SITE
/ note="Heterocyclic base guanine is attached to
N-acetyl (2- aminoethyl)glycine through the N-acetyl
group at position 9 of the base."

(ix) FEATURE:
(A) NAME/KEY: Modified-site
(B) LOCATION: 3
(D) OTHER INFORMATION: /label=MODIFIED-SITE
/ note="Heterocyclic base adenine is attached to N-
acetyl (2- aminoethyl)glycine through the N-acetyl
group at position 9 of the base."

(ix) FEATURE:
(A) NAME/KEY: Modified-site
(B) LOCATION: 4
(D) OTHER INFORMATION: /label=MODIFIED-SITE
/ note="Heterocyclic base cytosine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 5
(D) OTHER INFORMATION: /label=MODIFIED-SITE
/ note="Heterocyclic base thymine is attached to N-
acetyl (2- amidoethyl)glycine through the N-acetyl
group at position 1 of the base."

(xi) SEQUENCE DESCRIPTION: SEQ ID NO:7:

Gly  Xaa  Xaa  Xaa  Xaa
1                    5

(2) INFORMATION FOR SEQ ID NO:8:

(i) SEQUENCE CHARACTERISTICS:
(A) LENGTH: 5

( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Modified-site
( B ) LOCATION: 2
( D ) OTHER INFORMATION: /label=MODIFIED-SITE
/ note="Heterocyclic base guanine is attached to N-acetyl (2- aminoethyl)glycine through the N-acetyl group at position 9 of the base."

( i x ) FEATURE:
( A ) NAME/KEY: Modified-site
( B ) LOCATION: 3
( D ) OTHER INFORMATION: /label=MODIFIED-SITE
/ note="Heterocyclic base adenine is attached to 1-N-[N-(BOC)- 2-aminoethyl]-4-carboxy-2-azetidinone through the C-3 group at position 9 of the base."

( i x ) FEATURE:
( A ) NAME/KEY: Modified-site
( B ) LOCATION: 4
( D ) OTHER INFORMATION: /label=MODIFIED-SITE
/ note="Heterocyclic base cytosine is attached to N-acetyl (2-aminoethyl)glycine through the N-acetyl group at position 1 of the base."

( i x ) FEATURE:
( A ) NAME/KEY: Modified-site
( B ) LOCATION: 5
( D ) OTHER INFORMATION: /label=MODIFIED-SITE
/ note="Heterocyclic base thymine is attached to N-acetyl (2-amidoethyl)glycine through the N-acetyl group at position 1 of the base."

( x i ) SEQUENCE DESCRIPTION: SEQ ID NO:8:

Gly Xaa Xaa Xaa Xaa
1               5

( 2 ) INFORMATION FOR SEQ ID NO:9:

( i ) SEQUENCE CHARACTERISTICS:
( A ) LENGTH: 5
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Modified-site
( B ) LOCATION: 2
( D ) OTHER INFORMATION: /label=MODIFIED-SITE
/ note="Heterocyclic base guanine is attached to N-acetyl (2-aminoethyl)glycine through the N-acetyl group at position 9 of the base."

( i x ) FEATURE:
( A ) NAME/KEY: Modified-site
( B ) LOCATION: 3
( D ) OTHER INFORMATION: /label=MODIFIED-SITE
/ note="Heterocyclic base adenine is attached to N-acetyl (2- aminoethyl)glycine through the N-acetyl group at position 9 of the base."

( i x ) FEATURE:
( A ) NAME/KEY: Modified-site
( B ) LOCATION: 4
( D ) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

( i x ) FEATURE:
( A ) NAME/KEY: Modified-site (B) LOCATION: 5
(D) OTHER INFORMATION: /label=MODIFIED-SITE
/ note="Heterocyclic base cytosine is attached to N-
acetyl (2- amidoethyl)glycine through the N-acetyl
group at position 1 of the base."

(x i) SEQUENCE DESCRIPTION: SEQ ID NO:9:

Gly Xaa Xaa Xaa Xaa
1               5

(2) INFORMATION FOR SEQ ID NO:10:

(i) SEQUENCE CHARACTERISTICS:
(A) LENGTH: 5
(B) TYPE: amino acid
(C) STRANDEDNESS: single
(D) TOPOLOGY: unknown (i i) MOLECULE TYPE: peptide (i x) FEATURE:
(A) NAME/KEY: Modified-site
(B) LOCATION: 2
(D) OTHER INFORMATION: /label=MODIFIED-SITE
/ note="Heterocyclic base adenine is attached to N-
acetyl (2- aminoethyl)glycine through the N-acetyl
group at position 9 of the base."

(i x) FEATURE:
(A) NAME/KEY: Modified-site
(B) LOCATION: 3
(D) OTHER INFORMATION: /label=MODIFIED-SITE
/ note="Heterocyclic base thymine is attached to N-
acetyl (2- aminoethyl)glycine through the N-acetyl
group at position 1 of the base."

(i x) FEATURE:
(A) NAME/KEY: Modified-site
(B) LOCATION: 4
(D) OTHER INFORMATION: /label=MODIFIED-SITE
/ note="Heterocyclic base guanine is attached to 1-
N-[N-(BOC)- 2-aminoethyl]-4-carboxy-2-azetidinone
through the C-3 group at position 9 of the base."

(i x) FEATURE:
(A) NAME/KEY: Modified-site
(B) LOCATION: 5
(D) OTHER INFORMATION: /label=MODIFIED-SITE
/ note="Heterocyclic base cytosine is attached to N-
acetyl (2- amidoethyl)glycine through the N-acetyl
group at position 1 of the base."

(x i) SEQUENCE DESCRIPTION: SEQ ID NO:10:

Gly Xaa Xaa Xaa Xaa
1               5

(2) INFORMATION FOR SEQ ID NO:11:

(i) SEQUENCE CHARACTERISTICS:
(A) LENGTH: 11
(B) TYPE: amino acid
(C) STRANDEDNESS: single
(D) TOPOLOGY: unknown (i i) MOLECULE TYPE: peptide (i x) FEATURE:
(A) NAME/KEY: Modified-site
(B) LOCATION: 2
(D) OTHER INFORMATION: /label=MODIFIED-SITE
/ note="Heterocyclic base guanine is attached to N-
acetyl (2- aminoethyl)glycine through the N-acetyl
group at position 9 of the base."

(i x) FEATURE:
(A) NAME/KEY: Modified-site (B) LOCATION: 3
(D) OTHER INFORMATION: /label=MODIFIED-SITE
/ note="Heterocyclic base thymine is attached to N-acetyl (2- aminoethyl)glycine through the N-acetyl group at position 1 of the base."

(ix) FEATURE:
(A) NAME/KEY: Modified-site
(B) LOCATION: 4
(D) OTHER INFORMATION: /label=MODIFIED-SITE
/ note="Heterocyclic base adenine is attached to N-acetyl (2- aminoethyl)glycine through the N-acetyl group at position 9 of the base."

(ix) FEATURE:
(A) NAME/KEY: Modified-site
(B) LOCATION: 5
(D) OTHER INFORMATION: /label=MODIFIED-SITE
/ note="Heterocyclic base guanine is attached to N-acetyl (2- aminoethyl)glycine through to the N-acetyl group at position 1 of the base."

(ix) FEATURE:
(A) NAME/KEY: Modified-site
(B) LOCATION: 6
(D) OTHER INFORMATION: /label=MODIFIED-SITE
/ note="Heterocyclic base adenine is attached to N-acetyl (2- aminoethyl)glycine through the N-acetyl group at position 9 of the base."

(ix) FEATURE:
(A) NAME/KEY: Modified-site
(B) LOCATION: 7
(D) OTHER INFORMATION: /label=MODIFIED-SITE
/ note="Heterocyclic base thymine is attached to N-acetyl (2- aminoethyl)glycine through the N-acetyl group at position 1 of the base."

(ix) FEATURE:
(A) NAME/KEY: Modified-site
(B) LOCATION: 8
(D) OTHER INFORMATION: /label=MODIFIED-SITE
/ note="Heterocyclic base cytosine is attached to N-acetyl (2- aminoethyl)glycine through the N-acetyl the base."

(ix) FEATURE:
(A) NAME/KEY: Modified-site
(B) LOCATION: 9
(D) OTHER INFORMATION: /label=MODIFIED-SITE
/ note="Heterocyclic base adenine is attached to N-acetyl (2- aminoethyl)glycine through the N-acetyl group at position 9 of the base."

(ix) FEATURE:
(A) NAME/KEY: Modified-site
(B) LOCATION: 10
(D) OTHER INFORMATION: /label=MODIFIED-SITE
/ note="Heterocyclic base cytosine is attached to N-acetyl (2- aminoethyl)glycine through the N-acetyl group at position 1 of the base."

(ix) FEATURE:
(A) NAME/KEY: Modified-site
(B) LOCATION: 11
(D) OTHER INFORMATION: /label=MODIFIED-SITE
/ note="Heterocyclic base thymine is attached to N-acetyl (2- aminoethyl)glycine through the N-acetyl group at position 1 of the base."

(xi) SEQUENCE DESCRIPTION: SEQ ID NO:11:

```
Gly  Xaa  Xaa  Xaa  Xaa  Xaa  Xaa  Xaa  Xaa  Xaa  Xaa
 1                  5                        10
```

(2) INFORMATION FOR SEQ ID NO:12:

(i) SEQUENCE CHARACTERISTICS:
(A) LENGTH: 11

(B) TYPE: amino acid
(C) STRANDEDNESS: single
(D) TOPOLOGY: unknown (ii) MOLECULE TYPE: peptide (ix) FEATURE:
(A) NAME/KEY: Modified-site
(B) LOCATION: 2
(D) OTHER INFORMATION: /label=MODIFIED-SITE
/ note="Heterocyclic base adenine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 3
(D) OTHER INFORMATION: /label=MODIFIED-SITE
/ note="Heterocyclic base guanine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 4
(D) OTHER INFORMATION: /label=MODIFIED-SITE
/ note="Heterocyclic base thymine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 5
(D) OTHER INFORMATION: /label=MODIFIED-SITE
/ note="Heterocyclic base guanine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 6
(D) OTHER INFORMATION: /label=MODIFIED-SITE
/ note="Heterocyclic base adenine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site
(B) LOCATION: 7
(D) OTHER INFORMATION: /label=MODIFIED-SITE
/ note="Heterocyclic base thymine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 8
(D) OTHER INFORMATION: /label=MODIFIED-SITE
/ note="Heterocyclic base cytosine is attached to 1-
N-[N-(BOC)- 2-aminoethyl]-4-carboxy-2-azetidinone
through the C-3 group at position 1 of the base."

(ix) FEATURE:
(A) NAME/KEY: Modified-site
(B) LOCATION: 9
(D) OTHER INFORMATION: /label=MODIFIED-SITE
/ note="Heterocyclic base thymine is attached to
1-N-[N- (BOC)-2-aminoethyl]-4-carboxy-2-azetidinone
through the C-3 group at position 1 of the base."

(ix) FEATURE:
(A) NAME/KEY: Modified-site
(B) LOCATION: 10
(D) OTHER INFORMATION: /label=MODIFIED-SITE
/ note="Heterocyclic base adenine is attached to 1-
N-[N-(BOC)- 2-aminoethyl]-4-carboxy-2-azetidinone
through the C-3 group at position 9 of the base."

(ix) FEATURE:
(A) NAME/KEY: Modified-site (B) LOCATION: 11
(D) OTHER INFORMATION: /label=MODIFIED-SITE
     /note="Heterocyclic base cytosine is attached to 1-
     N-[N-(BOC)- 2-aminoethyl]-4-carboxy-2-azetidinone
     through the C-3 group at position 1 of the base."

(xi) SEQUENCE DESCRIPTION: SEQ ID NO:12:

```
Gly Xaa Xaa Xaa Xaa Xaa Xaa Xaa Xaa Xaa Xaa
1               5                       10
```

(2) INFORMATION FOR SEQ ID NO:13:

(i) SEQUENCE CHARACTERISTICS:
       (A) LENGTH: 25
       (B) TYPE: nucleic acid
       (C) STRANDEDNESS: single
       (D) TOPOLOGY: unknown (xi) SEQUENCE DESCRIPTION: SEQ ID NO:13:

```
GATCCCCCCA CCACGTGGTG CCTGA            25
```

(2) INFORMATION FOR SEQ ID NO:14:

(i) SEQUENCE CHARACTERISTICS:
       (A) LENGTH: 25
       (B) TYPE: nucleic acid
       (C) STRANDEDNESS: single
       (D) TOPOLOGY: unknown (xi) SEQUENCE DESCRIPTION: SEQ ID NO:14:

```
GATCTCAGGC ACCACGTGGT GGGGG            25
```

(2) INFORMATION FOR SEQ ID NO:15:

(i) SEQUENCE CHARACTERISTICS:
       (A) LENGTH: 21
       (B) TYPE: nucleic acid
       (C) STRANDEDNESS: single
       (D) TOPOLOGY: unknown (xi) SEQUENCE DESCRIPTION: SEQ ID NO:15:

```
CGCTTGGTGA CTCAGCCGGA A                21
```

(2) INFORMATION FOR SEQ ID NO:16:

(i) SEQUENCE CHARACTERISTICS:
       (A) LENGTH: 16
       (B) TYPE: nucleic acid
       (C) STRANDEDNESS: single
       (D) TOPOLOGY: linear (xi) SEQUENCE DESCRIPTION: SEQ ID NO:16:

```
GATCCAAAAA AAAAAG                      16
```

(2) INFORMATION FOR SEQ ID NO:17:

(i) SEQUENCE CHARACTERISTICS:
       (A) LENGTH: 16
       (B) TYPE: nucleic acid
       (C) STRANDEDNESS: single
       (D) TOPOLOGY: linear (xi) SEQUENCE DESCRIPTION: SEQ ID NO:17:

```
GATCCTTTTT TTTTTG                      16
```

(2) INFORMATION FOR SEQ ID NO:18:

(i) SEQUENCE CHARACTERISTICS:

( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO:18:

TCGACTTTTC TTTTTG 16

( 2 ) INFORMATION FOR SEQ ID NO:19:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO:19:

TCGACAAAAA GAAAAG 16

( 2 ) INFORMATION FOR SEQ ID NO:20:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO:20:

GAAGAAGAAA ACTGCA 16

( 2 ) INFORMATION FOR SEQ ID NO:21:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO:21:

GTTTCTTCT TCTGCA 16

( 2 ) INFORMATION FOR SEQ ID NO:22:

( i ) SEQUENCE CHARACTERISTICS:
( A ) LENGTH: 11
( B ) TYPE: amino acid
( C ) STRANDEDNESS: single
( D ) TOPOLOGY: unknown ( i i i ) MOLECULE TYPE: peptide ( i x ) FEATURE:
( A ) NAME/KEY: Modified-site
( B ) LOCATION: 2
( D ) OTHER INFORMATION: /label=MODIFIED-SITE
/ note="Heterocyclic base thymine is attached to 1-
N-[N-(BOC)- 2-aminoethyl]-4-carboxy-2-azetidinone
through the C-3 group at position 1 of the base."

( i x ) FEATURE:
( A ) NAME/KEY: Modified-site
( B ) LOCATION: 3
( D ) OTHER INFORMATION: /label=Modified-site
/ note="Heterocyclic base thymine is attached to 1-
N-[N-(BOC)- 2-aminoethyl]-4-carboxy-2-azetidinone
through the C-3 group at position 1 of the base."

( i x ) FEATURE:
( A ) NAME/KEY: Modified-site
( B ) LOCATION: 4
( D ) OTHER INFORMATION: /label=Modified-site
/ note="Heterocyclic base thymine is attached to 1-

N-[N-(BOC)- 2-aminoethyl]-4-carboxy-2-azetidinone
through the C-3 group at position 1 of the base."

(ix) FEATURE:
 (A) NAME/KEY: Modified-site
 (B) LOCATION: 5
 (D) OTHER INFORMATION: /label=Modified-site
  / note="Heterocyclic base thymine is attached to 1-
  N-[N-(BOC)- 2-aminoethyl]-4-carboxy-2-zetidinone
  through the C-3 group at position 1 of the base."

(ix) FEATURE:
 (A) NAME/KEY: Modified-site
 (B) LOCATION: 6
 (D) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

(ix) FEATURE:
 (A) NAME/KEY: Modified-site
 (B) LOCATION: 7
 (D) OTHER INFORMATION: /label=Modified-site
  / note="Heterocyclic base thymine is attached to
  1-N-[N- (BOC)-2-aminoethyl]-4-carboxy-2-azetidinone
  through the C-3 group at position 1 of the base."

(ix) FEATURE:
 (A) NAME/KEY: Modified-site
 (B) LOCATION: 8
 (D) OTHER INFORMATION: /label=Modified-site
  / note="Heterocyclic base thymine is attached to
  1-N-[N- (BOC)-2-aminoethyl]-4-carboxy-2-azetidinone
  through the C-3 group at position 1 of the base."

(ix) FEATURE:
 (A) NAME/KEY: Modified-site
 (B) LOCATION: 9
 (D) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

(ix) FEATURE:
 (A) NAME/KEY: Modified-site
 (B) LOCATION: 10
 (D) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

(ix) FEATURE:
 (A) NAME/KEY: Modified-site
 (B) LOCATION: 11
 (D) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

(xi) SEQUENCE DESCRIPTION: SEQ ID NO:22:

```
Gly Xaa Xaa Xaa Xaa Xaa Xaa Xaa Xaa Xaa Xaa
 1               5                       10
```

(2) INFORMATION FOR SEQ ID NO:23:

(i) SEQUENCE CHARACTERISTICS:
  (A) LENGTH: 9
  (B) TYPE: amino acid
  (C) STRANDEDNESS: single
  (D) TOPOLOGY: unknown (ii) MOLECULE TYPE: peptide (ix) FEATURE:
  (A) NAME/KEY: Modified-site
  (B) LOCATION: 2
  (D) OTHER INFORMATION: /label=MODIFIED-SITE
   / note="Heterocyclic base thymine is attached to 1-

N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 3
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 4
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 5
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 6
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 7
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 8
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(ix) FEATURE:
    (A) NAME/KEY: Modified-site
    (B) LOCATION: 9
    (D) OTHER INFORMATION: /label=Modified-site
    / note="Heterocyclic base thymine is attached to 1-
N-[N-(BOC)- 2-aminoethyl]-4-carboxy-2-azetidinone
through the C-3 group at position 1 of the base."

(xi) SEQUENCE DESCRIPTION: SEQ ID NO:23:

```
Gly  Xaa  Xaa  Xaa  Xaa  Xaa  Xaa  Xaa  Xaa
1                  5
```

(2) INFORMATION FOR SEQ ID NO:24:

(i) SEQUENCE CHARACTERISTICS:
        (A) LENGTH: 7
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /label=MODIFIED-SITE
        / note="Heterocyclic base thymine is attached to 1-

N-[N-(BOC)- 2-aminoethyl]-4-carboxy-2-azetidinone
through the C-3 group at position 1 of the base."

( i x ) FEATURE:
 ( A ) NAME/KEY: Modified-site
 ( B ) LOCATION: 3
 ( D ) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

( i x ) FEATURE:
 ( A ) NAME/KEY: Modified-site
 ( B ) LOCATION: 4
 ( D ) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

( i x ) FEATURE:
 ( A ) NAME/KEY: Modified-site
 ( B ) LOCATION: 5
 ( D ) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

( i x ) FEATURE:
 ( A ) NAME/KEY: Modified-site
 ( B ) LOCATION: 6
 ( D ) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

( i x ) FEATURE:
 ( A ) NAME/KEY: Modified-site
 ( B ) LOCATION: 7
 ( D ) OTHER INFORMATION: /label=Modified-site
  / note="Heterocyclic base thymine is attached to 1-
  N-[N-(BOC)- 2-aminoethyl]-4-carboxy-2-azetidinone
  through the C-3 group at position 1 of the base."

( x i ) SEQUENCE DESCRIPTION: SEQ ID NO:24:

Gly Xaa Xaa Xaa Xaa Xaa Xaa
 1     5

( 2 ) INFORMATION FOR SEQ ID NO:25:

( i ) SEQUENCE CHARACTERISTICS:
  ( A ) LENGTH: 16
  ( B ) TYPE: nucleic acid
  ( C ) STRANDEDNESS: single
  ( D ) TOPOLOGY: unknown ( x i ) SEQUENCE DESCRIPTION: SEQ ID NO: 25:

GATCCAAAAA AAAAAG  16

( 2 ) INFORMATION FOR SEQ ID NO:26:

( i ) SEQUENCE CHARACTERISTICS:
  ( A ) LENGTH: 6
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 2
  ( D ) OTHER INFORMATION: /label=MODIFIED-SITE
   / note="Heterocyclic base thymine is attached to 1-
   N-[N-(BOC)- 2-aminoethyl]-4-carboxy-2-azetidinone
   through the C-3 group at position 1 of the base."

( i x ) FEATURE:
    ( A ) NAME/KEY: Modified-site
    ( B ) LOCATION: 3
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 4
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 5
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 6
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( x i ) SEQUENCE DESCRIPTION: SEQ ID NO:26:

Gly  Xaa  Xaa  Xaa  Xaa  Xaa
    1                       5

( 2 ) INFORMATION FOR SEQ ID NO:27:

( i ) SEQUENCE CHARACTERISTICS:
        ( A ) LENGTH: 11
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 2
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

( i x ) FEATURE:
        ( A ) NAME/KEY: Modified-site
        ( B ) LOCATION: 3
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

( i x ) FEATURE:
        ( A ) NAME/KEY: Modified-site
        ( B ) LOCATION: 4
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

( i x ) FEATURE:
        ( A ) NAME/KEY: Modified-site
        ( B ) LOCATION: 5
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

( i x ) FEATURE:
    ( A ) NAME/KEY: Modified-site
    ( B ) LOCATION: 6
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 7
    ( D ) OTHER INFORMATION: /label=MODIFIED-SITE
        / note="Heterocyclic base cytosine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 8
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 9
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 10
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( i x ) FEATURE:
    ( A ) NAME/KEY: Modified-site
    ( B ) LOCATION: 11
    ( D ) OTHER INFORMATION: /label=MODIFIED-SITE
        / note="Heterocyclic base thymine is attached to 1-
        N-[N-(BOC)- 2-aminoethyl]-4-carboxy-2-azetidinone
        through the C-3 group at position 1 of the base."

( x i ) SEQUENCE DESCRIPTION: SEQ ID NO:27:

Gly  Xaa  Xaa  Xaa  Xaa  Xaa  Xaa  Xaa  Xaa  Xaa  Xaa
    1                     5                           10

( 2 ) INFORMATION FOR SEQ ID NO:28:

( i ) SEQUENCE CHARACTERISTICS:
        ( A ) LENGTH: 11
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 2
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

( i x ) FEATURE:
        ( A ) NAME/KEY: Modified-site
        ( B ) LOCATION: 3
        ( D ) OTHER INFORMATION: /label=MODIFIED-SITE
            / note="Heterocyclic base thymine is attached to 1-
            N-[N-(BOC)- 2-aminoethyl]-4-carboxy-2-azetidinone
            through the C-3 group at position 1 of the base."

(ix) FEATURE:
(A) NAME/KEY: Modified-site
(B) LOCATION: 4
(D) OTHER INFORMATION: /label=MODIFIED-SITE
/ note="Heterocyclic base cytosine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 5
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 6
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 7
(D) OTHER INFORMATION: /label=MODIFIED-SITE
/ note="Heterocyclic base cytosine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 8
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 9
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 10
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(ix) FEATURE:
(A) NAME/KEY: Modified-site
(B) LOCATION: 11
(D) OTHER INFORMATION: /label=MODIFIED-SITE
/ note="Heterocyclic base thymine is attached to 1-N-[N-(BOC)- 2-aminoethyl]-4-carboxy-2-azetidinone through the C-3 group at position 1 of the base."

(xi) SEQUENCE DESCRIPTION: SEQ ID NO:28:

Gly Xaa Xaa Xaa Xaa Xaa Xaa Xaa Xaa Xaa Xaa
1               5                   10

What is claimed is:

1. A compound having the structure:

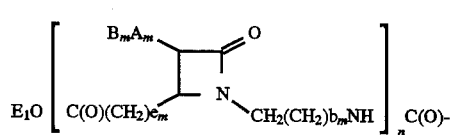

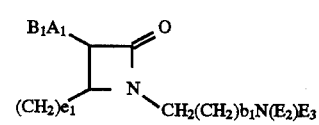

wherein

B$_1$ and each B$_m$, independently, are a naturally occurring nucleobase, a non-naturally occurring nucleobase, a DNA intercalator, a nucleobase-binding group, hydrogen, hydroxyl, a (C$_1$–C$_4$)alkanoyl, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, CF$_3$, OCF$_3$, OCN, O-alkyl, S-alkyl, N-alkyl, O-alkenyl, S-alkenyl, N-alkenyl, SOCH$_3$, SO$_2$CH$_3$, ONO$_2$, NO$_2$, N$_3$, NH$_2$, heterocycloalkyl, heterocycloalkaryl, aminoalkylamino, polyalkylamino or substituted silyl, an RNA cleaving group, or a reporter ligand;

A$_1$ and each A$_m$, independently are (CR$_6$R$_7$)$_x$ where R$_6$ and R$_7$ are independently selected from the group consisting of hydrogen, alkyl, aryl, aralkyl, heteroaryl, hydroxy, alkoxy, alkylthio, NR$_3$R$_4$ and SR$_5$, where each of R$_3$ and R$_4$ is independently selected from the group consisting of hydrogen, alkyl, alkoxy, or alkylthio-substituted alkyl, alkoxy, alkylthio and amino; and R$_5$ is hydrogen, alkyl, hydroxy-, alkoxy-, or alkylthio- substituted alkyl, or R$_6$ and R$_7$ taken together complete an alicyclic system, wherein said alkyl groups have from 1 to 6 carbons and said aryl groups have from 6 to 14 carbons;

$_x$ is 0 to 10, provided that when B$_1$ or B$_m$ are hydrogen or hydroxyl, $_x$ is not 0;

E$_1$ is a carboxyl protecting group or hydrogen;

E$_2$ and E$_3$, independently, are hydrogen, an amine protecting group, or taken together with N form a cyclic structure;

n is an integer from 1 to 60;

e$_1$ and each e$_m$, independently, are 0 or an integer from 1 to 6; and b$_1$ and each b$_m$, independently, are 0 or an integer from 1 to 6.

2. The compound of claim 1 wherein B$_1$ and each B$_m$, independently, are a naturally occurring nucleobase.

3. The compound of claim 1 wherein B$_1$ and each B$_m$, independently, are a non naturally occurring nucleobase.

4. The compound of claim 1 wherein n is from 1 to about 40.

5. The compound of claim 1 wherein n is from 1 to about 20.

6. The compound of claim 1 wherein e$_1$, e$_m$, b$_1$, and each b$_m$ are, independently, an integer from 1 to about 4.

7. A compound having the structure:

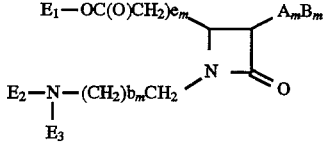

wherein:

B$_m$ is a naturally occurring nucleobase, a non-naturally occurring nucleobase, a DNA intercalator, a nucleobase-binding group, hydrogen, hydroxyl, a (C$_1$–C$_4$)alkanoyl, an aromatic moiety, or a heterocyclic moiety, which for groups other than hydrogen and hydroxyl may be optionally substituted with one or more additional functional groups selected from hydrogen, hydroxyl, alkyl, substituted alkyl, alkaryl or aralkyl, F, Cl, Br, CN, CF$_3$, OCF$_3$, OCN, O-alkyl, S-alkyl, N-alkyl, O-alkenyl, S-alkenyl, N-alkenyl, SOCH$_3$, SO$_2$CH$_3$, ONO$_2$, NO$_2$, N$_3$, NH$_2$, heterocycloalkyl, heterocycloalkaryl, aminoalkylamino, polyalkylamino or substituted silyl, an RNA cleaving group, or a reporter ligand;

A$_m$ is (CR$_6$R$_7$)$_x$ where R$_6$ and R$_7$ are independently selected from the group consisting of hydrogen, alkyl, aryl, aralkyl, heteroaryl, hydroxy, alkoxy, alkylthio, NR$_3$R$_4$ and SR$_5$, where each of R$_3$ and R$_4$ is independently selected from the group consisting of hydrogen, alkyl, alkoxy, or alkylthio-substituted alkyl, alkoxy, alkylthio and amino; and R$_5$ is hydrogen, alkyl, hydroxy-, alkoxy-, or alkylthio- substituted alkyl, or R$_6$ and R$_7$ taken together complete an alicyclic system, wherein said alkyl groups have from 1 to 6 carbons and said aryl groups have from 6 to 14 carbons;

$_x$ is 0 to 10, provided that when B$_m$ is hydrogen or hydroxyl, $_x$ is not 0;

E$_1$ is a carboxyl protecting group or hydrogen;

E$_2$ and E$_3$, independently, are hydrogen, an amine protecting group, or taken together with N form a cyclic structure;

e$_m$ is 0 or an integer from 1 to 6; and b$_m$ is 0 or an integer from 1 to 6.

8. The compound of claim 7 wherein B$_m$ is a naturally occurring nucleobase.

9. The compound of claim 7 wherein B$_m$ is a non-naturally occurring nucleobase.

10. The compound of claim 7 wherein e$_m$, and b$_m$ are independently an integer from 1 to about 4.

11. An oligomeric compound consisting of amide-linked β-lactam monomers, said monomers having N-1, C-3, and C-4 positions substituted with covalently bonded groups, wherein:

one of said N-1, C-3, and C-4 positions is substituted with a group having the formula:

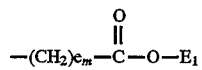

another of said N-1, C-3, and C-4 positions is substituted with a group having the formula:

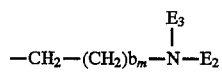

and the remaining of said N-1, C-3, and C-4 positions is substituted with a group having the formula:

wherein:

each A, independently, is (CR$_6$R$_7$)$_x$ where R$_6$ and R$_7$ are independently selected from the group consisting of hydrogen, alkyl, aryl, aralkyl, heteroaryl, hydroxy, alkoxy, alkylthio, NR$_3$R$_4$ and SR$_5$, where each of R$_3$ and R$_4$ is independently selected from the group consisting of hydrogen, alkyl, alkoxy, or alkylthio-substituted alkyl, alkoxy, alkylthio and amino; and R$_5$ is hydrogen, alkyl, hydroxy-, alkoxy-, or alkylthio-substituted alkyl, or R$_6$ and R$_7$ taken together complete an alicyclic system, wherein said alkyl groups have from 1 to 6 carbons and said aryl groups have from 6 to 14 carbons;

$x$ is 0 to 10;

each B, independently, is a naturally occurring nucleobase, or a non-naturally occurring nucleobase;

each $E_1$, independently, is a carboxyl protecting group or hydrogen;

each $E_2$ and each $E_3$, independently, is hydrogen, BOC-glycine, an amine protecting group, or taken together with N form a cyclic structure; and each e and each b, independently, is 0 or an integer from 1 to 6.

12. The oligomeric compound of claim 11 wherein $E_1$ is a carboxyl protecting group.

13. The oligomeric compound of claim 11 wherein $E_2$ is BOC-glycine or an amine protecting group.

14. The compound of claim 11 wherein one of said C-4 and said C-3 positions of said lactam monomers are substituted with said group having said formula:

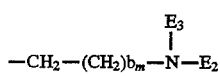

and b is 0.

15. The compound of claim 11 wherein each B is a naturally occurring nucleobase.

16. The compound of claim 11 wherein each B is a non-naturally occurring nucleobase.

17. The compound of claim 11 wherein said oligomeric compound is from 1 to about 60 of said β-lactam monomers in length.

18. The compound of claim 11 wherein said oligomeric compound is from 1 to about 40 of said β-lactam monomers in length.

19. The compound of claim 11 wherein said oligomeric compound is from 1 to about 20 of said β-lactam monomers in length.

20. The compound of claim 11 wherein each of said e and said b is independently from 1 to about 4.

* * * * *

UNITED STATES PATENT AND TRADEMARK OFFICE
CERTIFICATE OF CORRECTION

PATENT NO. : 5,629,152
DATED : May 13, 1997
INVENTOR(S) : Ravikumar et al.

It is certified that error appears in the above-identified patent and that said Letters Patent is hereby corrected as shown below:

OTHER PUBLICATIONS
Daniels et al., "Membranes as Solid Supports for Peptide Synthesis", Tetrahedron Lett. 1989. 4345-4348
Kemp and Hoyng, "New Protective Groups for Peptide Synthesis--I The BIC Group Base and Solvent Lability of the 5- Benzisoxazolymethyleneoxycarbonylamino Function"Tetrahedron, 1975 4624-4628

Col. 2, line 23, please delete "halices" and insert therefor --helices--;
Col. 4, line 29, please insert --$NO_2$-- before "$N_3$"and after "$ONO_2$";
Col. 8, (Scheme I), please insert --+-- under "$B_m A_m$";
Col. 9, line 16, please delete "i" after "232" ;
Col. 9, line 38, please delete "11" ;
Col. 9, line 63, please delete ":"(after 30), and insert therefor --,-- ;
Col. 11, line 64, please delete "Ber" and insert therefor --Bet-- ;
Col. 12, line 37, please delete "3:" after "1974";
Col. 14, line 36, please delete "2"and insert therefor --11--;
Col. 20, line 18, please delete "(bn)" and insert therefor --(bL)-- ;
Col. 23, line 17, please delete "1.S ml" and insert therefor --15 ml-- :

UNITED STATES PATENT AND TRADEMARK OFFICE
CERTIFICATE OF CORRECTION

PATENT NO. : 5,629,152
DATED : May 13, 1997
INVENTOR(S) : Ravikumar et al.

It is certified that error appears in the above-identified patent and that said Letters Patent is hereby corrected as shown below:

Col. 25, line 34, 35, & 36, please insert --≠-- after "(ΔS" and before "/R)" and after "(-ΔH )" and after "(SΔ" and before "/R)" and after "ΔS ";
Col. 25, line 54, "immunoabsorbant" should be --Immunoabsorbant-- ;
Col. 27, line 58, please delete "los/jun" and insert therefor --fos/jun-- ;
Col. 28, line 20, please delete "pTSC2" and insert therefor -- pT8C2-- ;
Col. 30, line, 59, please delete "pASG2" and insert therefor -- pA8G2-- ;
Col. 31, line 7, please delete "pASG2" and insert therefor --pA8G2-- ;
Col. 32, line 10, please delete " Tag" and insert therefor -- Taq-- ;
Col. 33, line 38, please delete "=" and insert therefor --$_2$-- .

Signed and Sealed this

Seventeenth Day of April, 2001

Attest:

NICHOLAS P. GODICI

Attesting Officer     Acting Director of the United States Patent and Trademark Office